(12) United States Patent
Li et al.

(10) Patent No.: US 8,951,961 B2
(45) Date of Patent: Feb. 10, 2015

(54) STRUCTURAL AND MECHANISTIC BASIS FOR NOVEL COMPOUND BIOSYNTHESIS USING 4-ELECTRON HEXOSE OXIDASE

(71) Applicant: Academia Sinica, Taipei (TW)

(72) Inventors: Tsung-Lin Li, Taipei (TW); Yu-Chen Liu, Taipei (TW); Yi-Shan Li, Taipei (TW); Syue-Yi Lyu, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/938,761

(22) Filed: Jul. 10, 2013

(65) Prior Publication Data

US 2013/0288955 A1 Oct. 31, 2013

Related U.S. Application Data

(63) Continuation of application No. 12/896,747, filed on Oct. 1, 2010, now Pat. No. 8,507,427.

(60) Provisional application No. 61/248,288, filed on Oct. 2, 2009.

(51) Int. Cl.
| | |
|---|---|
| *A01N 37/18* | (2006.01) |
| *A61K 38/04* | (2006.01) |
| *C07K 9/00* | (2006.01) |
| *A61K 38/14* | (2006.01) |

(52) U.S. Cl.
CPC *C07K 9/008* (2013.01); *A61K 38/14* (2013.01)
USPC ............................................................ 514/2.6

(58) Field of Classification Search
CPC ... A61K 38/00; C07K 14/705; C07K 2317/41
See application file for complete search history.

(56) References Cited

U.S. PATENT DOCUMENTS 8,507,427 B2    8/2013   Li et al.

FOREIGN PATENT DOCUMENTS

EP            255256         2/1988

OTHER PUBLICATIONS

U.S. Appl. No. 12/896,747, Non-Final Office Action, mailed Dec. 7, 2012, 7 pages.
Li et al., "A Unique Flavin Mononucleotide-Linked Primary Alcohol Oxidase for Glycopeptide A40926 Maturation", Journal of the American Chemical Society, vol. 129, No. 44, Nov. 7, 2007, pp. 13384-13385.

*Primary Examiner* — Marcela M Cordero Garcia
*Assistant Examiner* — Kaipeen Yang
(74) *Attorney, Agent, or Firm* — Lowe Hauptman & Ham, LLP

(57) ABSTRACT

A novel pharmaceutical composition comprising a compound of formula (I) is disclosed. The novel compound can include a pharmaceutically acceptable carrier. The invention further comprises methods for making compounds of formula (I) using Dbv29, and to the use of compound of formula (I) to treat bacterial infections.

30 Claims, 6 Drawing Sheets

Relationship of structure and activity

SEQUENCE LISTING

<160> NUMBER OF SEQ ID NOS: 1

<210> SEQ ID NO 1
<211> LENGTH: 523
<212> TYPE: PRT
<213> ORGANISM: Actinomycete Nonomuraea sp

<400> SEQUENCE: 1

```
Met Thr Gly Gly Thr Gly Ala Asp Ala Ala Ser Ala Gly Ala Ser Ser
1               5                   10                  15

Thr Arg Pro Glu Leu Arg Gly Glu Arg Cys Leu Pro Pro Ala Gly Pro
            20                  25                  30

Val Lys Val Thr Pro Asp Asp Pro Arg Tyr Leu Asn Leu Lys Leu Arg
            35                  40                  45

Gly Ala Asn Ser Arg Phe Asn Gly Glu Pro Asp Tyr Ile His Leu Val
        50                  55                  60

Gly Ser Thr Gln Gln Val Ala Asp Ala Val Glu Glu Thr Val Arg Thr
65                  70                  75                  80

Gly Lys Arg Val Ala Val Arg Ser Gly Gly His Cys Phe Glu Asp Phe
                85                  90                  95

Val Asp Asn Pro Asp Val Lys Val Ile Ile Asp Met Ser Leu Leu Thr
            100                 105                 110

Glu Ile Ala Tyr Asp Pro Ser Met Asn Ala Phe Leu Ile Glu Pro Gly
        115                 120                 125

Asn Thr Leu Ser Glu Val Tyr Glu Lys Leu Tyr Leu Gly Trp Asn Val
        130                 135                 140

Thr Ile Pro Gly Gly Val Cys Gly Gly Val Gly Val Gly Gly His Ile
145                 150                 155                 160

Cys Gly Gly Gly Tyr Gly Pro Leu Ser Arg Gln Phe Gly Ser Val Val
                165                 170                 175

Asp Tyr Leu Tyr Ala Val Glu Val Val Val Asn Lys Gln Gly Lys
        180                 185                 190

Ala Arg Val Ile Val Ala Thr Arg Glu Arg Asp Asp Pro His His Asp
            195                 200                 205

Leu Trp Trp Ala His Thr Gly Gly Gly Gly Asn Phe Gly Val Val
        210                 215                 220

Thr Lys Tyr Trp Met Arg Val Pro Glu Asp Val Gly Arg Asn Pro Glu
225                 230                 235                 240

Arg Leu Leu Pro Lys Pro Pro Ala Thr Leu Leu Thr Ser Thr Val Thr
            245                 250                 255

Phe Asp Trp Ala Gly Met Thr Glu Ala Ala Phe Ser Arg Leu Leu Arg
        260                 265                 270

Asn His Gly Glu Trp Tyr Glu Arg Asn Ser Gly Pro Asp Ser Pro Tyr
        275                 280                 285

Thr Gly Leu Trp Ser Gln Leu Met Ile Gly Asn Glu Val Pro Gly Met
        290                 295                 300

Gly Glu Ser Gly Phe Met Met Pro Ile Gln Val Asp Ala Thr Arg Pro
305                 310                 315                 320

Asp Ala Arg Arg Leu Leu Asp Ala His Ile Glu Ala Val Ile Asp Gly
            325                 330                 335

Val Pro Pro Ala Glu Val Pro Glu Pro Ile Glu Gln Arg Trp Leu Ala
            340                 345                 350
```

```
Ser Thr Pro Gly Arg Gly Gly Arg Gly Pro Ala Ser Lys Thr Lys Ala
        355             360             365
Gly Tyr Leu Arg Lys Arg Leu Thr Asp Arg Gln Ile Gln Ala Val Tyr
        370             375             380
Glu Asn Met Thr His Met Asp Gly Ile Asp Tyr Gly Ala Val Trp Leu
385             390             395             400
Ile Gly Tyr Gly Gly Lys Val Asn Thr Val Asp Pro Ala Ala Thr Ala
                405             410             415
Leu Pro Gln Arg Asp Ala Ile Leu Lys Val Asn Tyr Ile Thr Gly Trp
            420             425             430
Ala Asn Pro Gly Asn Glu Ala Lys His Leu Thr Trp Val Arg Lys Leu
        435             440             445
Tyr Ala Asp Val Tyr Ala Glu Thr Gly Gly Val Pro Val Pro Asn Asp
    450             455             460
Val Ser Asp Gly Ala Tyr Ile Asn Tyr Pro Asp Ser Asp Leu Ala Asp
465             470             475             480
Pro Gly Leu Asn Thr Ser Gly Val Pro Trp His Asp Leu Tyr Tyr Lys
            485             490             495
Gly Asn His Pro Arg Leu Arg Lys Val Lys Ala Ala Tyr Asp Pro Arg
        500             505             510
Asn His Phe His His Ala Leu Ser Ile Arg Pro
        515             520
```

STRUCTURAL AND MECHANISTIC BASIS FOR NOVEL COMPOUND BIOSYNTHESIS USING 4-ELECTRON HEXOSE OXIDASE

CROSS REFERENCE TO RELATED APPLICATIONS

The present application is a continuation application of co-pending U.S. patent application Ser. No. 12/896,747, filed on Oct. 1, 2010, which claimed benefit to U.S. Patent Application No. 61/248,288 filed on Oct. 2, 2009, both of which are hereby incorporated by reference in their entirety.

FIELD OF THE INVENTION

The invention relates to novel pharmaceutical compounds, and more particularly to novel pharmaceutical compounds useful in treating bacterial infections.

BACKGROUND OF THE INVENTION

Over the last 50 years, the number of pathogenic and commensal bacterial strains resistant to antibiotics, and the number of antibiotics to which they are resistant have increased dramatically. As a result, infections that once were readily treatable by antibiotics may no longer be responsive to such treatments. Bacteria that develop resistance to antimicrobial treatments, such as methicillin-resistant *Staphylococcus aureus* (MRSA) and vancomycin-resistan *Enterococcus* (VRE), is a well-recognized medical problem world-wide and has become one of the most important threats to modern health care.

For decades, vancomycin has outpaced the multidrug resistance of MRSA. It is now facing increased resistance by emerging vancomycin-intermediate *S. aureus* (VISA) and vancomycin-resistan *Enterococcus*. New antimicrobial agents and improved methods are thus needed for the treatment and prevention of infections caused by such pathogens.

SUMMARY OF THE INVENTION

The present invention relates to a novel compound, which has the formula (I):

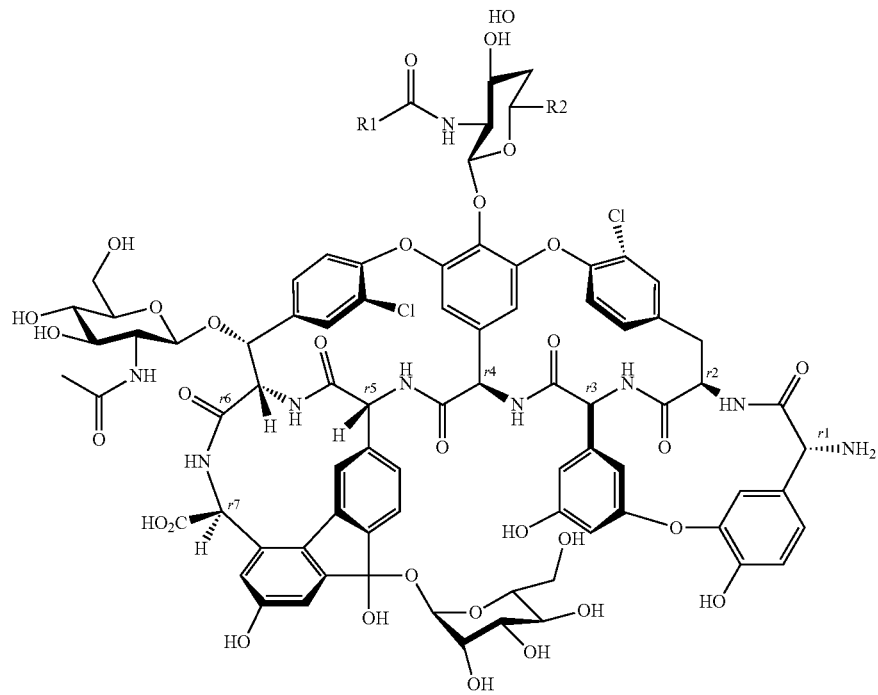

or a pharmaceutically acceptable salt thereof,
wherein
$R_1$ is selected from the group consisting of aryl, alkyl, alkynyl;
$R_2$ is selected from the group consisting of C(O)OH, C(O)NH—$R_3$, and $CH_2$—NH—$R_4$;
wherein
$R_3$ is selected from the group consisting of aryl, alkyl, alkynyl;
$R_4$ is selected from the group consisting of aryl, alkyl, alkynyl, adamantyl, and $C_1$-$C_{10}$ azide.

The invention also provides a pharmaceutical composition comprising a compound of formula (I) and a pharmaceutical acceptable carrier. Another aspect of the present invention relates to a flavoenzyme, Dbv29, and the catalytic functions of Dbv29 in the preparation of the novel compound of the present invention.

Another aspect of this invention provides a method of treating a subject (e.g., humans and other mammals) with a bacterial infection. The method comprises the step of administering to a subject in need thereof an effective amount of the compound of formula (I). The compound of formula (I) can be administered by any of the accepted modes of administration including inhalation, topical, oral, rectal, implanted reservoir and parenteral (such as intravenous, intramuscular, subcutaneous, intra-articular, intra-synovial, cisternal, intrathecal, intrahepatic, intralesional and intracranial). Parenteral administration is preferred.

DETAILED DESCRIPTION OF THE INVENTION

Novel Compound of Formula (I)

Figure 1A:
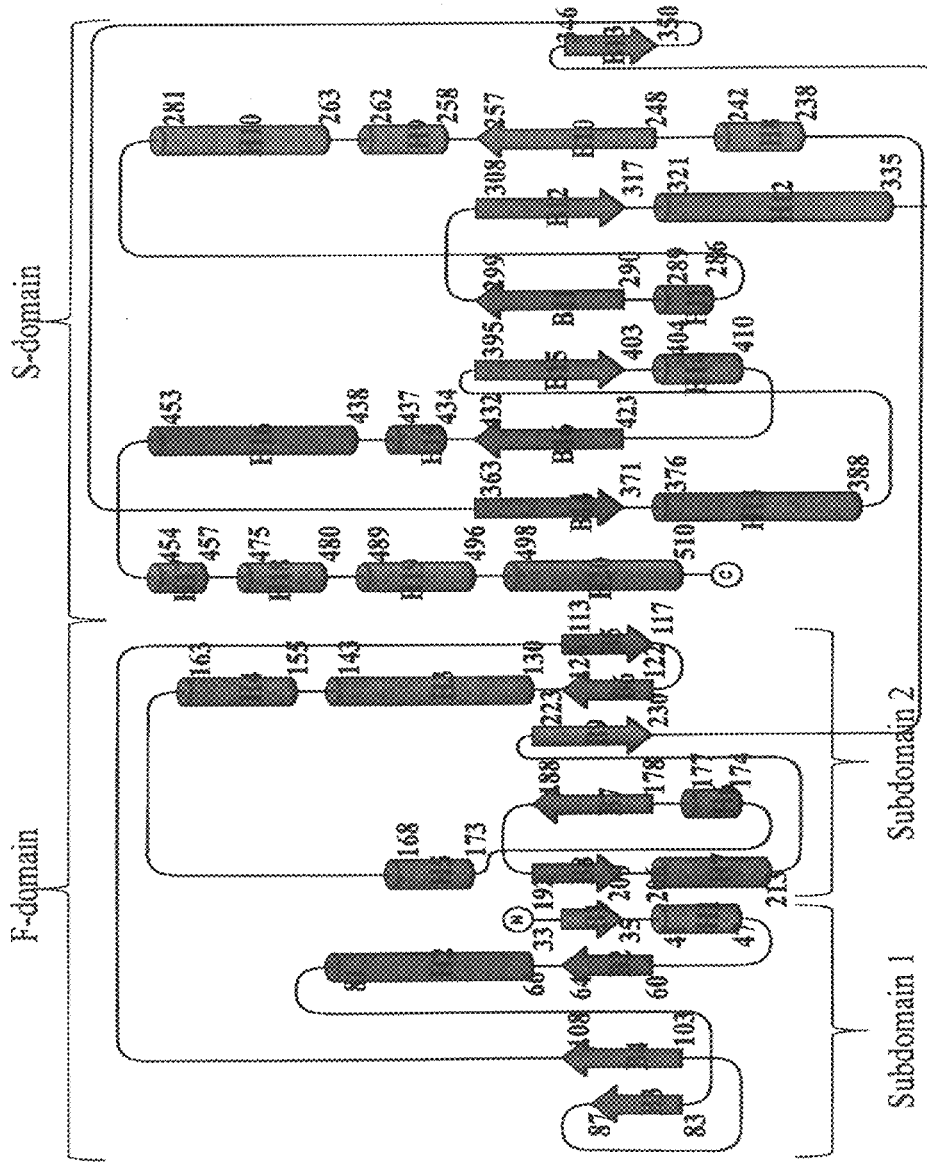
FIG. 1(a) shows the overall structure of Dbv29.

The present invention relates to a novel compound, which has the formula (I)

If $R_4$ is selected from alkynyl or azide, the compound can be converted to other analogs through click chemistry for other applications such as identification of a second mode of action for broader spectrum analogs.

"Alkyl" refers to groups of from 1 to 15 carbon atoms inclusively, either straight chained, branched, cyclic or unsaturated, more preferably from 1 to 10 carbon atoms inclusively.

The term "aryl" is used herein to refer to an aromatic carbocyclic group of 6 to 14 carbon atoms inclusively having a single ring (e.g. phenyl) or multiple condensed rings (e.g., naphthyl or anthryl). Preferred aryl include phenyl and benzyl.

"Azide" refers to an anion with the formula $N_3^-$.

"Alkynyl" refers to groups of from 2 to 6 carbon atoms inclusively, either straight or branched containing at least one triple bond.

The pharmaceutically acceptable salts of the compounds of formula (I) include the non-toxic salts formed from non-toxic inorganic or organic bases. For example, non-toxic salts can be formed with inorganic bases such as an alkali or alkaline earth metal hydroxide, e.g., potassium, sodium, lithium, calcium, or magnesium; and with organic bases such as an amine.

The pharmaceutically acceptable salts of the compounds of formula (I) include non-toxic salts formed from non-toxic

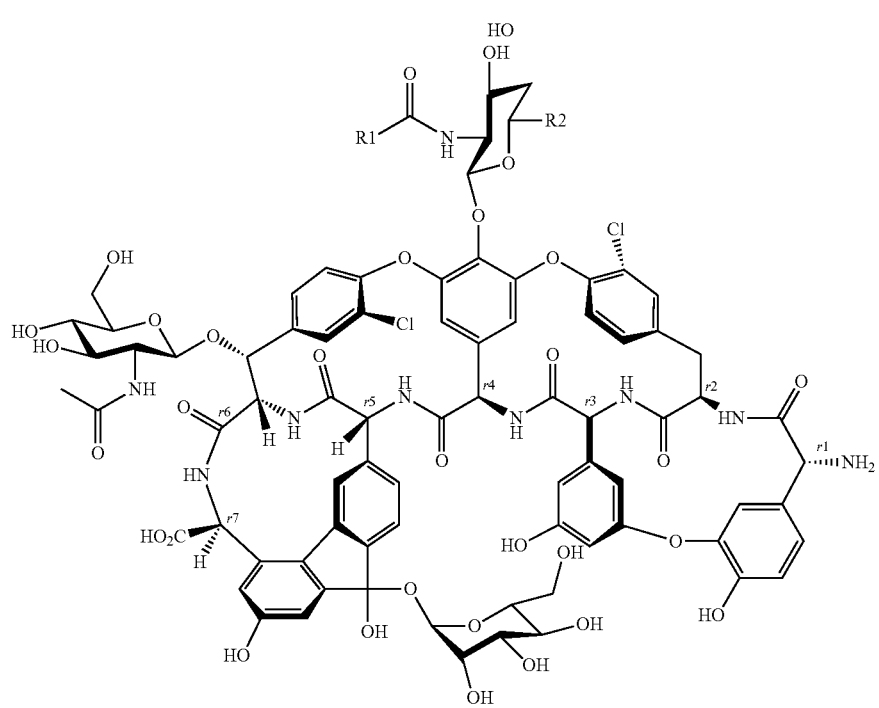

(I)

or a pharmaceutically acceptable salt thereof,
wherein
$R_1$ is selected from the group consisting of aryl, alkyl, alkynyl;
$R_2$ is selected from the group consisting of C(O)OH, C(O)NH—$R_3$, and $CH_2$—NH—$R_4$;
wherein
$R_3$ is selected from the group consisting of aryl, alkyl, alkynyl;
$R_4$ is selected from the group consisting of aryl, alkyl, alkynyl, adamantyl, and $C_1$-$C_{10}$ azide.

inorganic or organic acids. Example of organic and inorganic acids are, for example, hydrochloric, sulfuric, phosphoric, acetic, succinic, citric, lactic, maleic, fumaric, palmitic, cholic, pamoic, mucic, D-glutamic, glutaric, glycolic, phthalic, tartaric, lauric, stearic, salicylic, sorbic and benzoic acids.

The pharmaceutically acceptable salts can be synthesized from the compounds of formula (I) by any conventional chemical methods. In one embodiment, the salt is prepared by reacting the free acid with a requisite amount of inorganic or organic base in a suitable solvent or various combinations of solvents. In another embodiment, the salt is prepared by reacting the free base with a requisite amount of inorganic or organic acid in a suitable solvent or various combinations of solvents.

In a preferred embodiment, $R_1$ is $(CH3)_2—CH—(CH_2)_6$ and $R_2$ is $CH_2—NH—CH_2—C_6H_6$.

the Pharmaceutical Composition

The present invention is also directed to a pharmaceutical composition comprising the compound of formula (I) and a pharmaceutically acceptable carrier.

A "pharmaceutically acceptable carrier" refers to a carrier that, after administration to or upon a subject, does not cause undesirable physiological effects. The carrier in a pharmaceutical composition must be "acceptable" also in the sense that is compatible with the active ingredient and, preferably, capable of stabilizing it. Suitable pharmaceutically acceptable carriers are well known in the art and vary with the desired form and mode of administration of the pharmaceutical composition. For example, they may include, but are not limited to, biocompatible vehicles, adjuvants, additives (such as pH-adjusting additives), diluents or excipients such as fillers, binders, wetting agents, disintegrators, surface-active agents, lubricants and the like. One or more pharmaceutical carriers may be used for the delivery of a compound of formula (I).

The pharmaceutical composition can be prepared for inhalation, topical, oral, rectal, implanted reservoir and parenteral delivery (such as intravenous, intramuscular, subcutaneous, intra-articular, intra-synovial, cisternal, intrathecal, intrahepatic, intralesional and intracranial).

The pharmaceutical composition can be prepared by any method known in the art of pharmacy. Such methods include the step of bringing into association the active compound with one or more carriers. For instance, to prepare compositions suitable for injection, solutions and suspensions are sterilized and are preferably isotonic to blood. In making injectable preparations, carriers which are commonly used in this field are used, for example, water, ethyl alcohol, propylene glycol. In these instances, adequate amounts of isotonicity adjusters such as sodium chloride, glucose or glycerin can be added to make the preparations isotonic. The aqueous sterile injection solution may further comprise oxidants, buffers, and other similar additions, which are acceptable for parenteral compositions.

For instance, for oral administration in the form of a tablet or capsule, the active compound can be comminuted with a pharmaceutically acceptable carrier such as ethanol, glycerol, water and the like. Powders are prepared by comminuting the compound to a suitable fine size and mixing it with a comminuted pharmaceutical carrier such as an edible carbohydrate, for example, starch or mannitol. Flavoring, dispersing and coloring agents can also be present.

For the treatment of the eyes or other external tissues, for example, the mouth and the skin, the pharmaceutical compositions are preferably applied as a topical ointment or cream. When formulated in an ointment, the active compound may be employed with either a paraffinic or a water-miscible ointment base. Alternatively, the active compound may be formulated in a cream with an oil-in-water cream base or a water-in-oil base.

The Flavoenzyme Dbv29

The present invention is also directed to a flavoenzyme, Dbv29, and the catalytic function of the enzyme in the preparation of the novel compound of formula (I). Dbv29 is a flavin dinucleotide (FAD)-dependent primary alcohol glycopeptide hexose oxidase which carries out a 4-electron oxidation reaction. The four-electron oxidation reaction from primary alcohol to acid catalyzed by Dbv29 was disclosed in *J Am Chem Soc* 129:13384-13385 (2007) by Li et al, which is incorporated herein by reference. Dbv29 catalyses the last step of the N-acyl aminoglucuronyl biosynthesis. Dbv29 can be obtained from a filamentous actinomycete *Nonomuraea* sp. ATCC39727 and its amino acid sequence is listed in Table 1 (SEQ ID NO:1). The structure of Dbv 29 and the complex structure of Dbv29 have been deposited in the Protein Data Bank under accession numbers 2wdw and 2wdx, respectively.

TABLE 1

| | | | | | |
|---|---|---|---|---|---|
| 1 mtggtgadaa | sagasstrpe | lrgerclppa | gpvkvtpddp | rylnlklrga | nsrfngepdy |
| 61 ihlvgstqqv | adaveetvrt | gkrvavrsgg | hcfedfvdnp | dvkviidmsl | lteiaydpsm |
| 121 nafliepgnt | lsevyeklyl | gwnvtipggv | cggvgvgghi | cgggygplsr | qfgsvvdyly |
| 181 avevvvvnkq | gkarvivatr | erddphhdlw | wahtgggggn | fgvvtkywmr | vpedvgrnpe |
| 241 rllpkppatl | ltstvtfdwa | gmteaafsrl | lrnhgewyer | nsgpdspytg | lwsqlmigne |
| 301 vpgmgesgfm | mpiqvdatrp | darrlldahi | eavidgvppa | evpepieqrw | lastpgrggr |
| 361 gpasktkagy | lrkrltdrqi | qavyenmthm | dgidygavwl | igyggkvntv | dpaatalpqr |
| 421 dailkvnyit | gwanpgneak | hltwvrklya | dvyaetggvp | vpndvsdgay | inypdsdlad |
| 481 pglntsgvpw | hdlyykgnhp | rlrkvkaayd | prnhfhhals | irp | |

It differs from other hexose oxidoreductases in the coenzyme used and in lacking a typical Cys residue in the active site.

Two domains for the catalytic activity are identified, i.e., the F domain (residues 1-230), which binds FAD and the S domain (residues 235-523), which recognizes the substrate.

Figure 1B:
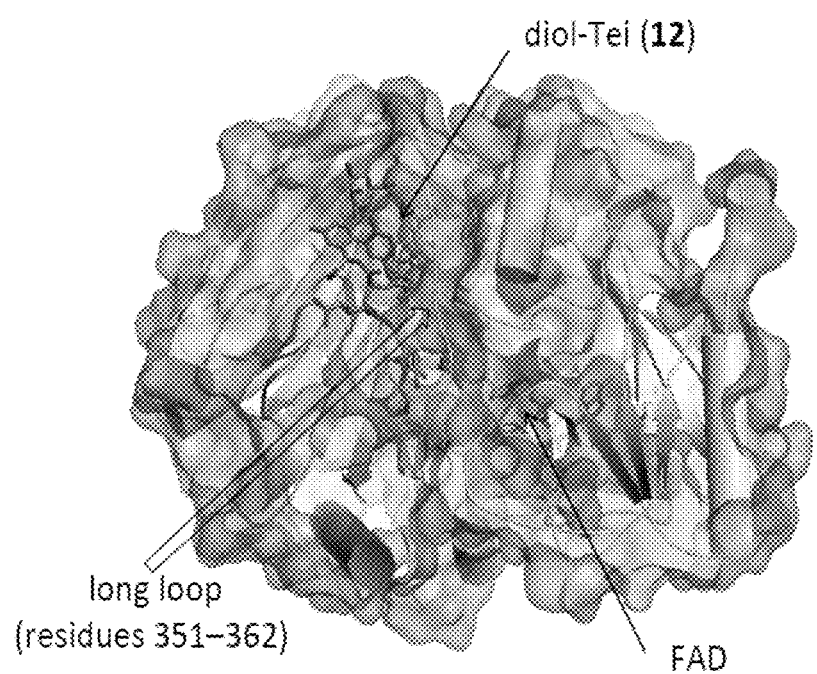
FIG. 1(b) shows the long-loop region crossing over the binding pocket of Dbv29.
Figure 1C:
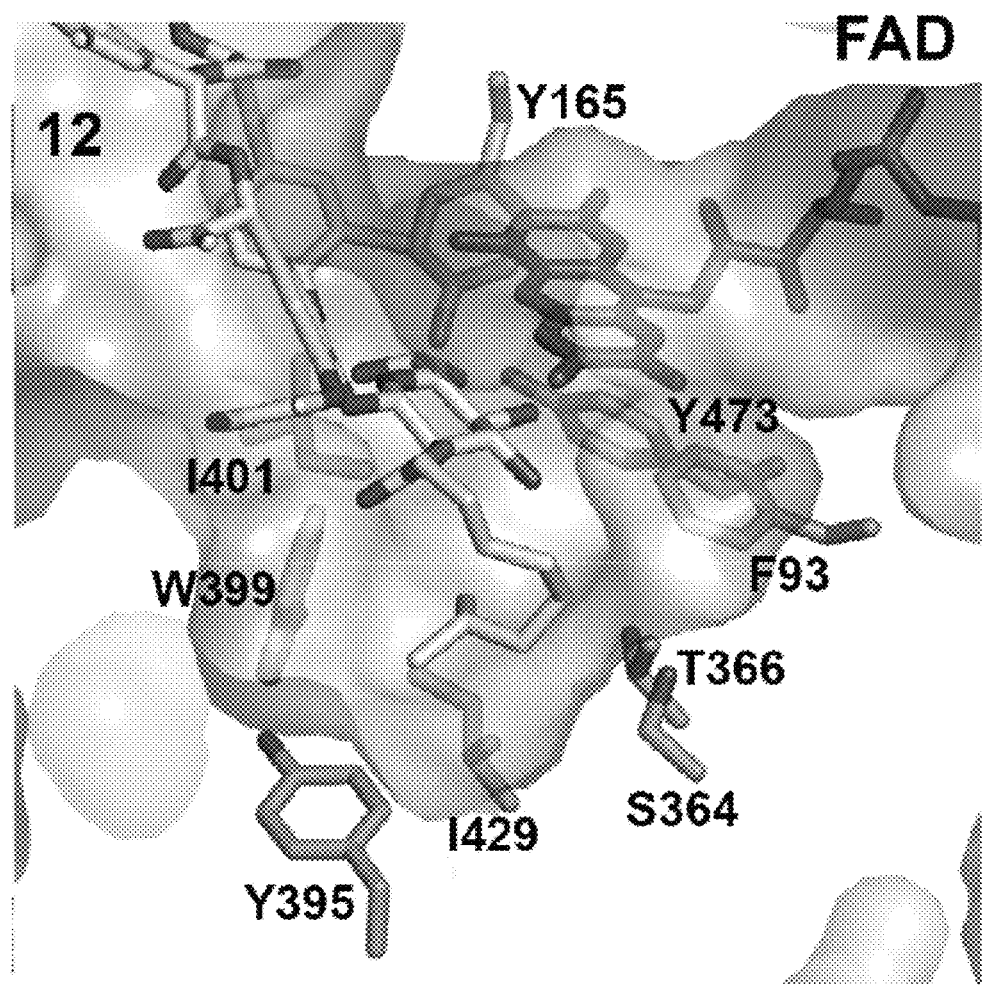
FIG. 1(c) shows the lipid cavity of Dbv29.

See FIG. 1. The F domain can be further divided into two subdomains. The first subdomain 1 (the N-terminal subdomain (residues 1-105) consists of a central four-stranded β-sheet (B1-B4 with the strand order of 1, 2, 4, 3, wherein B1 runs antiparallel to the others), sandwiched on each side by one α-helix (H1 and H2); the second subdomain 2 (residues 113-163 and 165-230) consists of a β-sheet of five antiparallel strands (B5-B9 with the strand order of 5, 6, 9, 7, 8) that faces against five irregular α-helices (H3, H4, H6, H7 and H20). For the S domain, this domain is composed of an extended antiparallel seven-stranded β-sheet (B10-B16 with the strand order of 13, 10, 12, 11, 15, 16, 14), faced by four major α-helices in a row (H12, H10, H13, and H16). (See FIG. 1) These two domains are joined by two long-loop regions (residues 231-241 and 454-474).

Figure 2:
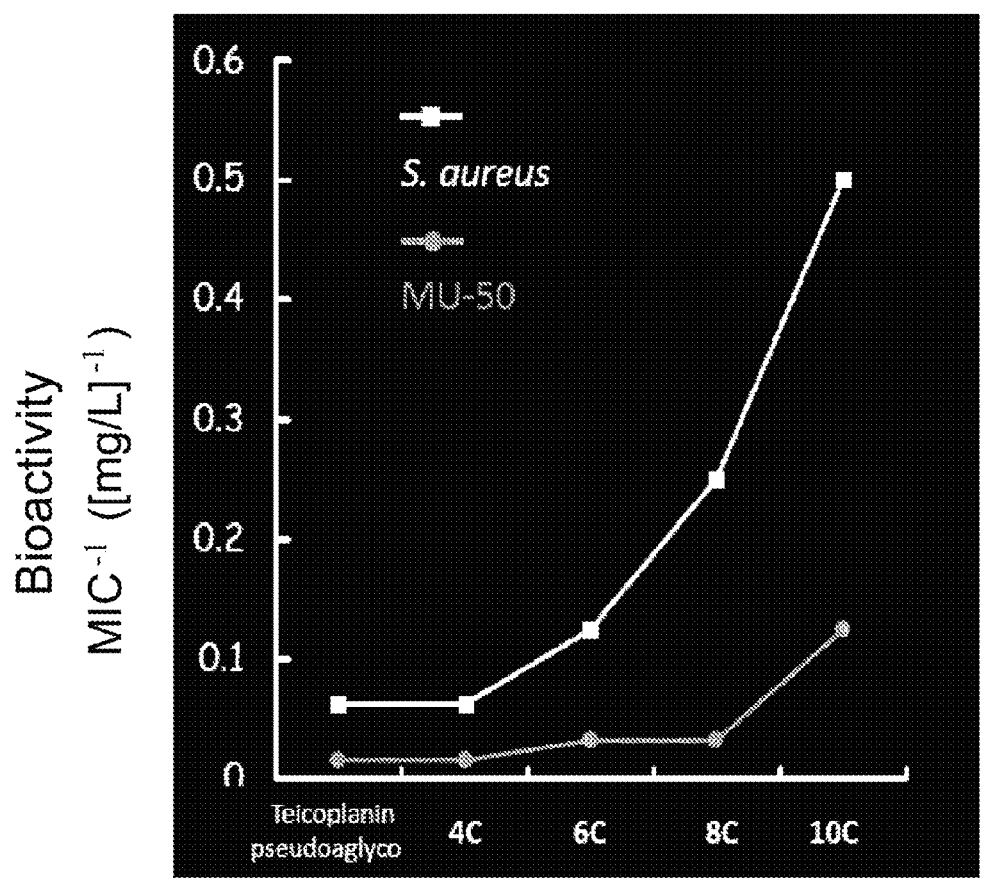
FIG. 2 shows the result of a Structure-Activity Relationship study. The experimental result indicates that the compound of formula (I) with a longer side chain has a better antibacterial activity against *Staphylococcus Aureus*.

A long-loop region (residues 351-362) crosses over the binding pocket. (See FIG. 1(b).) The N-acyl moiety of the amino sugar is inserted further into a hydrophobic lipid cavity, which is formed by residues Phe-93, Ser-364, Tyr-395, Trp-399 and Ile-429. (See FIG. 1(c).) A longer acyl side chain is favored to pack into the lipid cavity, as the longer the side chain the better the anti-bacterial activity ($C_{10}$ vs $C_4$, by >10 folds, see FIG. 2). The sugar ring anchors against the si face of the isoalloxazine ring of FAD and exposes carbon atom $C_5$ close to the $N_5$ nitrogen of FAD. The hydroxyl group of $C_4$ forms hydrogen bonds with Asn-427. The hydroxyl group of $C_6$ interacts with the side chains of Tyr-165 and Tyr-473. Most of residues that line the ligand-binding site are located in different loop regions.

Several ligand-binding residues of Dbv29 were identified. Trp-399 is nearby the reducing end of the sugar, and, together with Ile-401, stands above the shoulder of the r4 sugar head and poises the head facing the isoalloxazine ring. Trp-399 was determined to be catalytically important as no product was produced by the W399A mutant, while the W399F mutant retained 15% activity (Table 2). Thus, a bulkier and hydrophobic side chain may be favored at the position. Ile-401 that stands on the other side of the sugar head, nearby the $C_6$ carbon, is also influential as the activity was significantly reduced when this residue was mutated to smaller Ala (9%) or bulkier Trp (2%, Table 2). Thr-366 that situates opposite Trp-399 at the entry of the lipid cavity may assist the lipid chain insertion into the lipid cavity. Two mutants (T366A and T366E) showed reduced activities (11% and 5% relative activity, respectively; Table 2). Ser-364, lining at the bottom of the cavity, may force the lipid to fold in a spiral manner. The enzyme activity was reduced significantly when it was changed to bigger and charged side chains (S364K/R, Table 2).

TABLE 2

Relative enzymatic activities of Dbv29 mutants

| Mutants | Expression | Flavinylation/ FAD binding | Relative activity[a] | Rationale | Outcome |
|---|---|---|---|---|---|
| C26A | + | + | 1.11 | Putative point of active site general base | Role disproven |
| C92A | + | + | 0.95 | Putative point of active site general base | Role disproven |
| C151A | + | + | 0.23 | Putative point of active site general base/ Putative point of covalent attachment | Role disproven/ Role proven |
| C161A | + | + | 0.84 | Putative point of active site general base | Role disproven |
| H91A | + | + | 0.11 | Putative point of covalent attachment | Role proven |
| I401A | + | + | 0.09 | Potential ligand-binding residue | Role proven |
| I401W | + | + | 0.02 | Potential ligand-binding residue | Role proven |
| N44A | + | + | 0.87 | Potential interface interacting residue | Role proven |
| R41A | + | + | 0.72 | Potential interface interacting residue | Role proven |
| R360E | + | + | 0.76 | Putative point affecting FAD attachment | Role disproven |
| R360L | + | + | 0.23 | Putative point affecting FAD attachment | Role disproven |
| S364K | + | + | 0.04 | Potential ligand-binding residue/ Putative point affecting FAD attachment | Role proven/ Role disproven |
| S364R | + | + | 0.08 | Potential ligand-binding residue/ Putative point affecting FAD attachment | Role proven/ Role disproven |
| T366A | + | + | 0.11 | Potential ligand-binding residue/ Putative point affecting FAD attachment | Role proven/ Role disproven |
| T366E | + | + | 0.05 | Potential ligand-binding residue/ Putative point affecting FAD attachment | Role proven/ Role disproven |
| T366L | + | + | 0.13 | Potential ligand-binding residue/ Putative point affecting FAD attachment | Role proven/ Role disproven |
| W399A | + | + | — | Potential ligand-binding residue | Role proven |
| W399F | + | + | 0.16 | Potential ligand-binding residue | Role proven |
| Y135F | − | − | — | Putative point affecting FAD attachment | Role disproven |
| Y165F | + | + | 0.70 | Putative point of active site general base | Role proven |

TABLE 2-continued

Relative enzymatic activities of Dbv29 mutants

| Mutants | Expression | Flavinylation/ FAD binding | Relative activity[a] | Rationale | Outcome |
|---|---|---|---|---|---|
| Y165W | + | + | 0.03 | Putative point of active site general base | Role proven |
| Y370F | + | + | 0.10 | Putative point affecting FAD attachment | Role disproven |
| Y403F | + | + | 0.65 | Putative point affecting FAD attachment | Role disproven |
| Y428F | + | + | 1.00 | Putative point affecting FAD attachment | Role disproven |
| Y453F | + | + | 0.82 | Putative point affecting FAD attachment | Role disproven |
| Y470F | + | + | 0.21 | Putative point affecting FAD attachment | Role disproven |
| Y473F | + | + | 0.23 | Putative point of active site general base | Role proven |
| Y473E | + | + | — | Putative point of active site general base | Role proven |
| H91A/C151A | + | + | 0.05 | Putative point of covalent attachment | Role proven |
| R41A/N44A | + | + | 0.59 | Potential interface interacting residue | Role proven |
| R360E/T366E | + | + | 0.03 | Putative point affecting FAD attachment | Role disproven |
| R360L/T366A | + | + | 0.03 | Putative point affecting FAD attachment | Role disproven |
| R360L/T366E | + | + | 0.01 | Putative point affecting FAD attachment | Role disproven |
| Y165F/Y473F | + | − | — | Putative point of active site general base | Role proven |
| Y428F/Y453F | + | + | 1.08 | Putative point affecting FAD attachment | Role disproven |
| Y370F/Y403F | + | + | 0.05 | Putative point affecting FAD attachment | Role disproven |

The analyses of Dbv29 also shows that Tyr-473 and Tyr-165 function as a unique "molecular device" that governs cofactor binding, catalysis, and folding of the enzyme.

Cofactor Binding.

Even though the isoalloxazine ring of flavin is covalently linked to the side chains of His-91 and Cys-151, binding of FAD is governed by the tyrosine pair. Single mutants (H91A and C151A) retain 11% and 23% activities, respectively, relative to WT, and the double mutant (H91A/C151A) also retains 5% activity (Table 2) as well as the yellow color. On the other hand, Y165F/Y473F double mutation (but not the two single mutations) led to loss of the yellow color and total loss of catalytic activity (Table 2).

Active Site Structures and Catalysis.

Despite the crystal being grown with Teicoplanin, the density best fitted is neither Teicoplanin (substrate) nor oxo-Teicoplanin (product). It is a water-coordinated diol species because two electron densities on the $C_6$ terminus of the amino sugar 12 (See Scheme 1) share equal weighting in $sp^3$ configuration, thus the structure of the complex represents the transformed substrate for the second half of the oxidation. It also provides a structural basis for a proposed catalytic mechanism: in the initial stage the $C_6$ hydroxyl group is most likely de-protonated by the hydroxyl group of Tyr-473 that is activated by the hydroxyl group of Tyr-165. This pair together drives the pro-R hydride transfer from the $C_6$ carbon to the $N_5$ nitrogen of isoalloxazine ring. The hydroxyl group of Tyr-165 is further facilitated by the diol-coordinated water molecule in the second oxidation stage, where a proton relay network is formed amid the tyrosine pair, the substrate diol and a water molecule.

To further support that the Y165-Y473 pair functions as a molecular device, it is necessary to show that no other di-hydroxy pairs around the active site possess similar properties. Four other tyrosine residues, Tyr-135, -370, -403 and -470, which cluster together nearby the active site, were individually mutated to Phe. These mutants (except Y135F that could not be expressed) did not lose FAD, although the enzyme activities vary (Table 2). When the distance between two hydroxyl groups is extended to 5 Å, two extra tyrosine pairs fall within this scope, which are Y403/Y370 (4.1 Å) and Y428/Y453 (2.8 Å). The double mutants, Y403F/Y370F and Y428F/Y453F, were constructed and shown to contain bicovalent FAD and retain enzyme activities (Table 2). In addition to these 'in cis' residue pairs, residue pairs 'in trans' (side chains point in opposite directions) other than tyrosine were also examined. Thr-366 that gates at the lipid cavity, along with the bulky and charged Arg-360 which sits on the same long loop (351-362) but face in opposite direction were selected. Five mutants were made, which include two single mutations R360E/T366E. The FAD was retained in all mutants, and the double mutations displayed a synergistic negative effect on overall enzyme activity (Table 2). Taken together, the results support that the tyrosine pair (Tyr-165 and -473) is unique in functioning as a molecular device.

the Processes of Producing the Compounds of Formula (I)

The compound of formula (I) is prepared using teicoplanin as a starting material. Teicoplanin is a glycopeptide antibiotic for treating serious infections caused by Gram-positive bacteria, including methicillin-resistant *Staphylococcus aureus* and *Enterococcus faecalis*. It is commercially available and can be prepared by known methods, for example, U.S. Pat. No. 7,192,743, which is incorporated herein by reference. The amount of teicoplanin used is not critical, although a concentration of about 0.1 mM to about 5 mM is preferred.

The crystal structure of the Dbv29-oxo-Tei complex indicates another important property—that the aldehyde group (its diol adduct)—is highly exposed. This can explain that, when the reaction was performed in $^{18}$O-water, both oxygens of the diol intermediate are labeled with $^{18}$O. In addition, when reactions containing Tei with/without Dbv29 were carried out in a NaBD$_4$-containing solution, MS analyses of the Tei recovered from the reaction (a mixture of unreacted Tei and Tei obtained from reduction of the aldehyde intermediate) clearly showed M+1. This showed the possibility of trapping and modifying the aldehyde intermediate as a way to produce compounds of formula (I)).

Compounds of formula (I) can be prepared according to Scheme 1, which comprises: (a) binding teicoplanin 4 to Dbv29; and (b) incubating the mixture (a).

Scheme 1

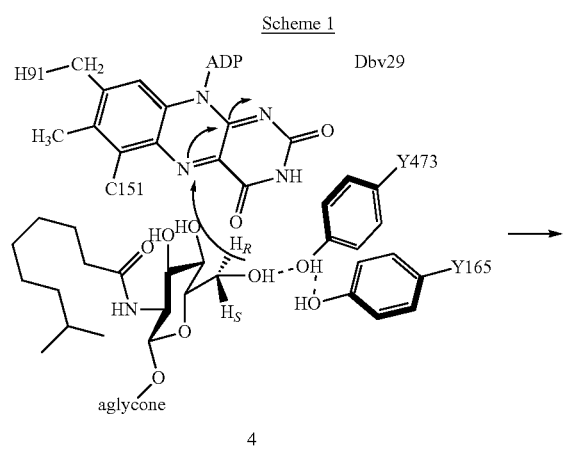

4

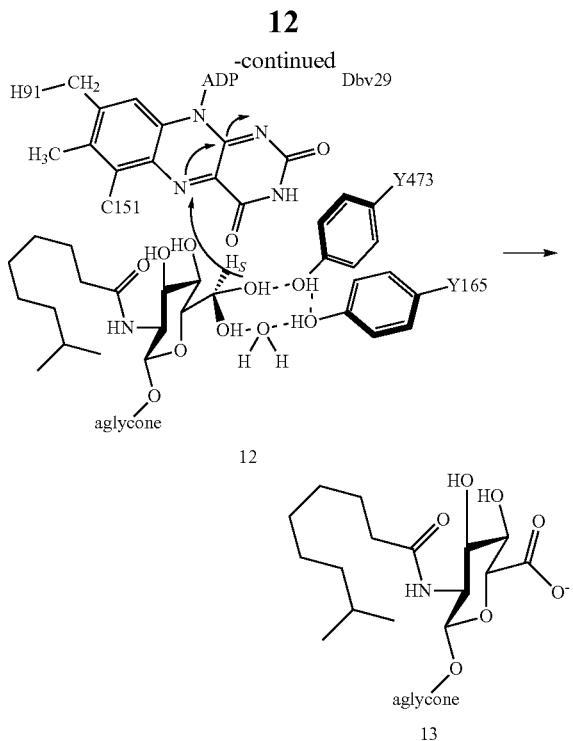

-continued

12

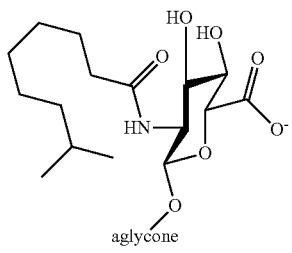

aglycone

13

The incubation temperature ranges from about 30° C. to about 40° C., and preferably about 37° C. The incubation time ranges from about 1 hour to 10 hours, and preferably about 3 hours to 4 hours.

Compounds of formula (I) can also be prepared according to Scheme 2, comprising: (a) binding teicoplanin 4 to Dbv29; (b) adding $C_{1-6}$ alkylamine to mixture (a); and (c) incubating the mixture (b).

Scheme 2

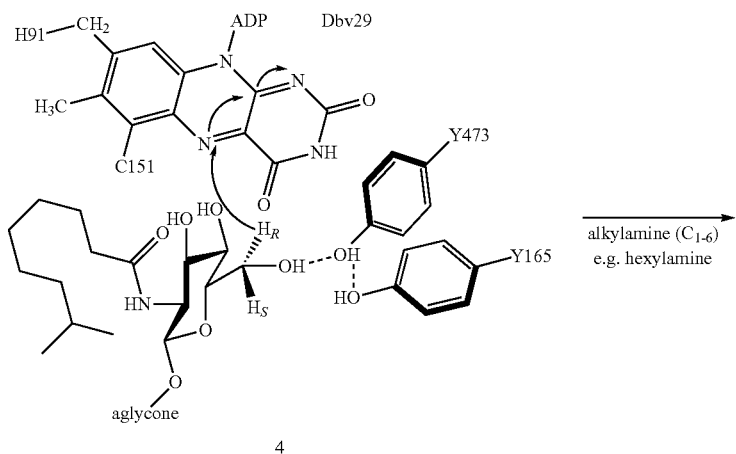

4

-continued

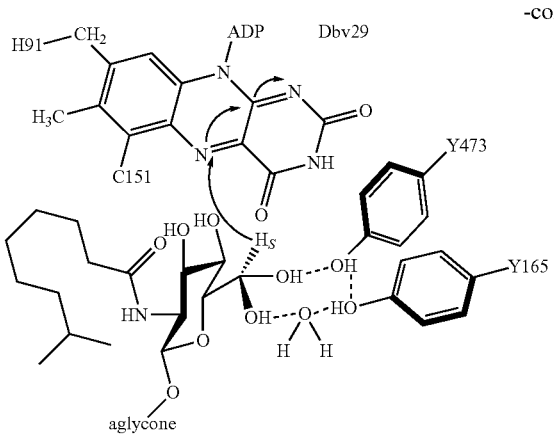

12

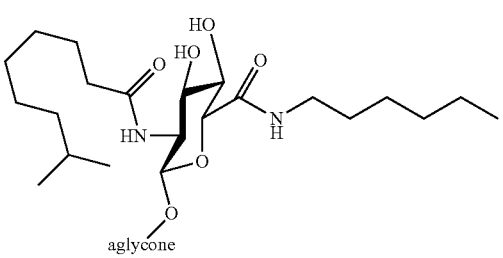

15

About 5 mM to about 15 mM of $C_{1-6}$ alkylamine can be used. The $C_{1-6}$ alkylamine may react with the aldehyde intermediate as soon as it is formed in the first oxidation reaction, the resulting gem-hydroxyl-$C_{1-6}$ alkylamine may then undergo the second oxidation reaction without leaving the active site of Dbv29. The incubation temperature ranges from about 30° C. to about 40° C., and preferably about 37° C. The incubation time ranges from about 1 hour to about 48 hours, preferably about 5 hours to about 24 hours, and more preferably about 16 hours.

Compound of formula (I) can also be prepared according to Scheme 3, comprising: (a) binding teicoplanin 4 to Dbv29; (b) adding $C_{6-15}$ alkylamine, a reducing agent, and an organic solvent to mixture (a); and (c) incubating the mixture (b).

Scheme 3

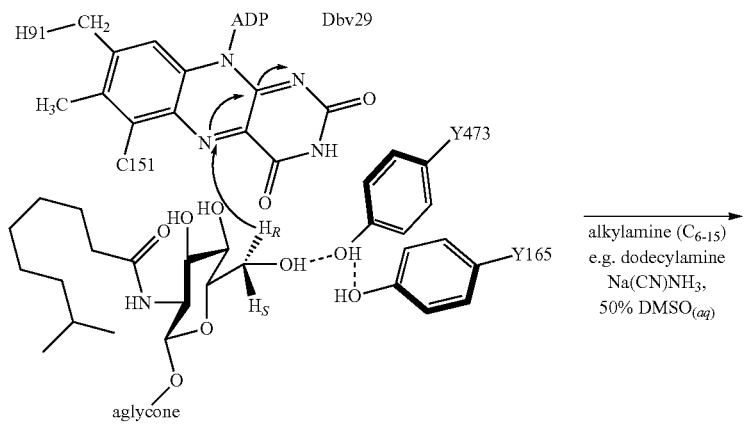

4

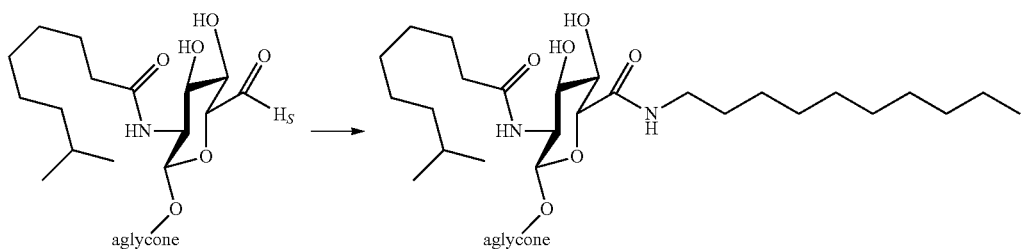

11 → 14

About 5 mM to about 15 mM of $C_{6-15}$ alkylamine can be used in this reaction. $C_{6-15}$ alkylamine maybe be too bully to enter the active site of Dbv29 so that $C_{6-15}$ alkylamine reacts with the aldehyde functional group in solution to form imine that is subsequently reduced by cyanohybridoborate (Na(CN)BH$_3$). The organic solvent used in Scheme 3 is DMSO. In one embodiment, about 10% to about 90% of DMSO is used. In a preferred embodiment, about 50% of DMSO is used.

The reducing agent used in Scheme 3 is cyanohydridoborate. In one embodiment, about 1 mM to about 20 mM of cyanohydridoborate is used. In a preferred embodiment, about 10 mM of cyanohydridoborate is used. The incubation temperature ranges from about 30° C. to about 40° C., and preferably about 37° C. The incubation time ranges from about 1 hour to about 48 hours, preferably about 5 hours to about 24 hours, and more preferably about 16 hours.

Compound of formula (I) can also be prepared according to Scheme IV, comprising: (a) binding teicoplanin 4 to Dbv21 and the mixture is incubated to form compound 5; (b) Combining compound 5 with Dbv8 and CoA derivatives, and the mixture is incubated; and (c) Combining mixture (b) with Dbv29 and O$_2$ as the electron acceptor, and the mixture is incubated.

Dbv21 is an enzyme which catalyses the hydrolysis of acetyl from N-acetyl glucosamine moiety. The deacetylation reaction by Dbv8 and the formation of compound 5 were described by Ho et al in *J Am Chem Soc* 128:13694-13694 (2006), which is incorporated herein by reference. Dbv8 is an enzyme which catalyses the acylation of glucosamine moiety with various CoA derivatives. The amino acid sequences of Dbv21 and Dbv8 were reported in *Chem Biol* 10(6): 541-549 (2003) by Sosio et al, which are incorporated herein by reference.

CoA derivatives are selected from the group comprising acetyl CoA, propionyl CoA, butyryl CoA, hexanoyl CoA, octanoyl CoA, decanoyl CoA, lauroyl CoA, myristoyl CoA, palmitoyl CoA, crotonyl CoA, isobutyryl CoA, isovaleryl CoA, malonyl CoA, succinyl CoA, glutaryl CoA, methylmalonyl CoA, acetoacetyl CoA, benzoyl CoA, phenylacetyl CoA, biphenylacetyl CoA, and naphthoacetyl CoA. The incubation temperature for Scheme 4 ranges from about 30° C. to about 40° C., and preferably about 37° C. The incubation times for steps (a) and (b) in Scheme 4 depend on the concentration of teicoplanin. In Step (a), for each mM of teicoplanin used, the incubation time ranges from about 1 hour to about 24 hours, and preferably about 6 hours. In Step (b), for each mM of teicoplanin used, the incubation time ranges from about 2 hours to about 12 hours, and preferably about 4 hours. The incubation time for step (c) in Scheme 4 ranges from about 1 hour to about 10 hours, and preferably about 3 hours to about 4 hours.

The present invention is also directed to a method of producing compound of formula (I) according to Scheme 5, comprising: (a) binding teicoplanin 4 to Dbv21 and the mixture is incubated to form compound 5; (b) Combining compound 5 with Dbv8 and CoA derivatives, and the mixture is incubated; and (c) Combining mixture (b) with Dbv29, O$_2$ as the electron acceptor, and alkylamine and the mixture is incubated.

Scheme 4

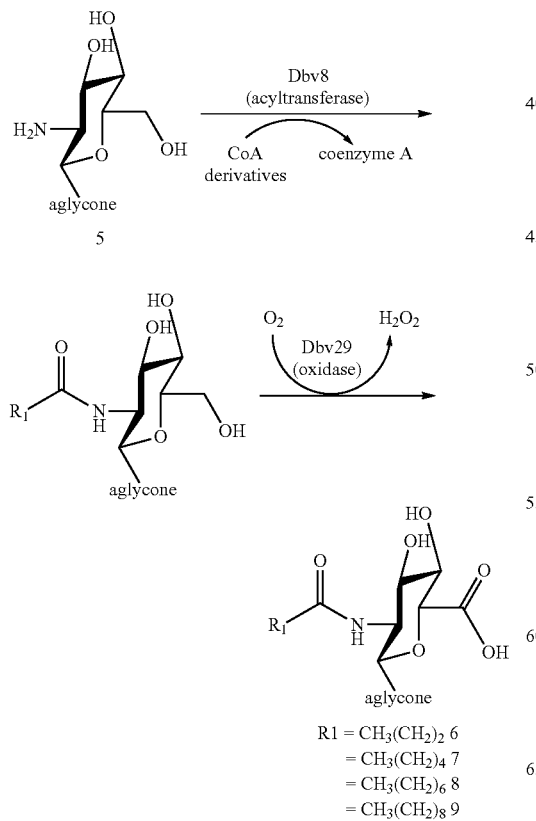

R1 = CH$_3$(CH$_2$)$_2$ 6
   = CH$_3$(CH$_2$)$_4$ 7
   = CH$_3$(CH$_2$)$_6$ 8
   = CH$_3$(CH$_2$)$_8$ 9

Scheme 5

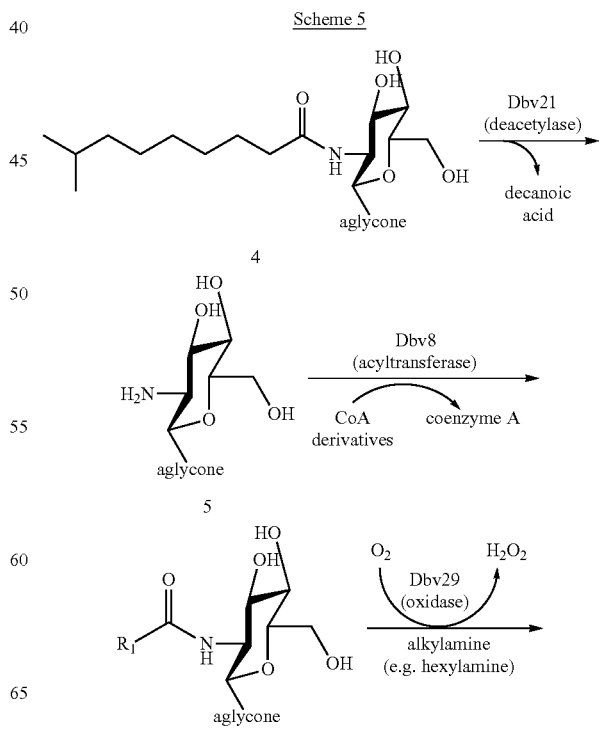

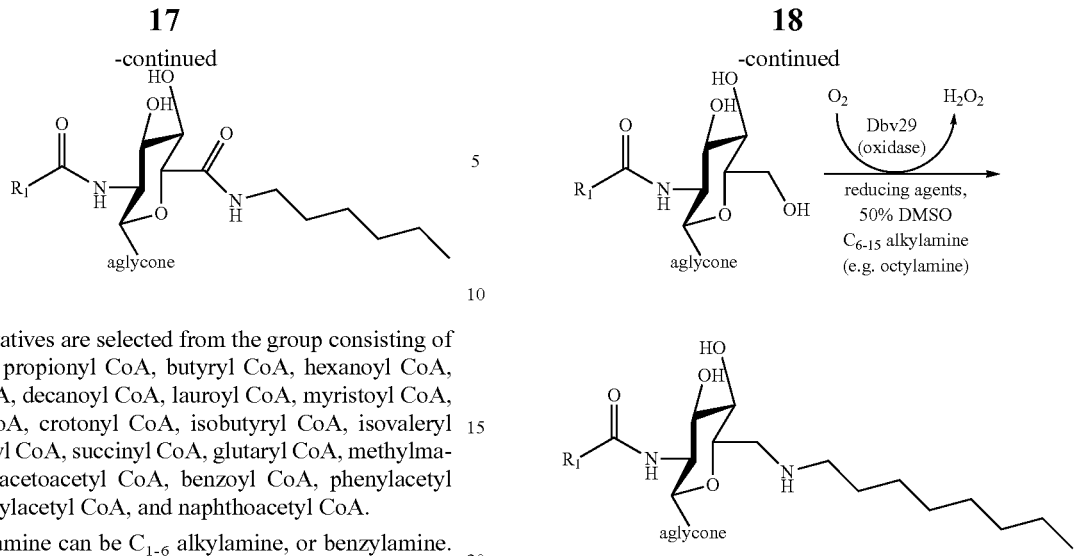

CoA derivatives are selected from the group consisting of acetyl CoA, propionyl CoA, butyryl CoA, hexanoyl CoA, octanoyl CoA, decanoyl CoA, lauroyl CoA, myristoyl CoA, palmitoyl CoA, crotonyl CoA, isobutyryl CoA, isovaleryl CoA, malonyl CoA, succinyl CoA, glutaryl CoA, methylmalonyl CoA, acetoacetyl CoA, benzoyl CoA, phenylacetyl CoA, biphenylacetyl CoA, and naphthoacetyl CoA.

The alkylamine can be $C_{1-6}$ alkylamine, or benzylamine. About 5 mM to about 15 mM of alkylamine can be used in this reaction. The incubation temperature ranges from about 30° C. to about 40° C., and preferably about 37° C. The incubation times for steps (a), (b) and (c) in Scheme 5 depend on the concentration of teicoplanin. In Step (a), for each mM of teicoplanin used, the incubation time ranges from about 1 hour to about 24 hours, and preferably about 6 hours. In Step (b), for each mM of teicoplanin used, the incubation time ranges from about 2 hours to about 12 hours, and preferably about 4 hours. In Step (c), for each mM of teicoplanin used, the incubation time ranges from about 1 hour to about 48 hours, preferably about 5 hours to about 24 hours, and more preferably about 16 hours.

Compounds of formula (I) can also be prepared according to Scheme 6, comprising: (a) binding teicoplanin 4 to Dbv21 and the mixture is incubated to form compound 5; (b) Combining compound 5 with Dbv8 and CoA derivatives, and the mixture is incubated: and (c) Combining mixture (b) with Dbv29, $O_2$ as the electron acceptor, alkylamine, an organic solvents and a reducing agents, and the mixture is incubated.

Scheme 6

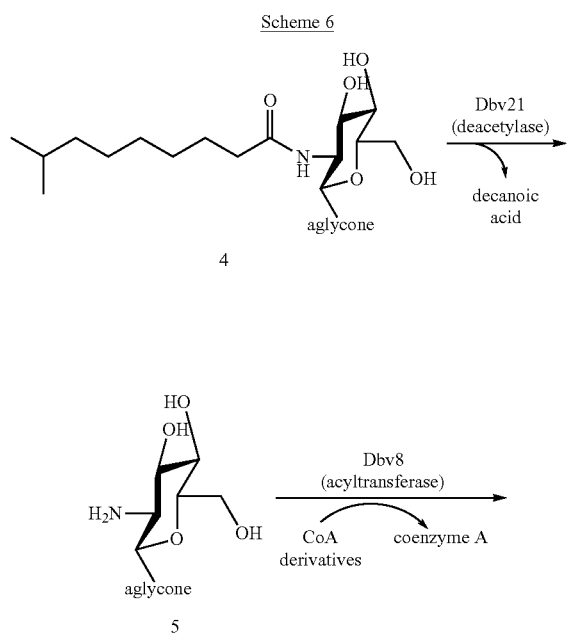

CoA derivatives are selected from the group consisting of acetyl CoA, propionyl CoA, butyryl CoA, hexanoyl CoA, octanoyl CoA, decanoyl CoA, lauroyl CoA, myristoyl CoA, palmitoyl CoA, crotonyl CoA, isobutyryl CoA, isovaleryl CoA, malonyl CoA, succinyl CoA, glutaryl CoA, methylmalonyl CoA, acetoacetyl CoA, benzoyl CoA, phenylacetyl CoA, biphenylacetyl CoA, and naphthoacetyl CoA.

The alkylamine in Scheme 6 is $C_{6-15}$ alkylamine or benzylamine. About 5 mM to about 15 mM of alkylamine can be used in this reaction. The organic solvent used in Scheme 6 is DMSO. In one embodiment, about 10% to about 90% of DMSO is used. In a preferred embodiment, about 50% of DMSO is used.

The reducing agent used in Scheme 6 is cyanohydridoborate. In one embodiment, about 1 mM to about 20 mM of cyanohydridoborate is used. In a preferred embodiment, about 10 mM of cyanohydridoborate is used. The incubation temperature for Scheme 6 ranges from about 30° C. to about 40° C., and preferably about 37° C.

The incubation times for Steps (a) and (b) in Scheme 6 depend on the concentration of teicoplanin. In Step (a), for each mM of teicoplanin used, the incubation time ranges from about 1 hour to 24 hours, and preferably about 6 hours. In step (b), for each mM of teicoplanin used, the incubation time ranges from about 2 hours to about 12 hours, and preferably about 4 hours. The incubation time for step (c) in Scheme 6 ranges from about 1 hour to about 48 hours, preferably about 5 hours to about 24 hours, and more preferably about 16 hours.

the Method of Treating a Bacterial Infection

The method of treating a bacterial infection in a subject in need of such treatment, comprises the administration of an effective amount of the compound of formula (I) and a pharmaceutically acceptable salt thereof.

The in vitro antibacterial activity of the compound of formula (I) against classically "resistant" strains is superior to vancomycin and teicoplanin. The minimum inhibitory concentration (MIC) value against VRE for compounds of formula (I) can be 8 to 32 folds lower than that of vancomycin and teicoplanin (see Table 6). In one embodiment, the method includes administering to a subject an effective amount of the compound of formula (I) against the vancomycin-susceptible enterococcus infection. In another embodiment, the method includes administering to a subject an effective amount of the active compound against the vancomycin-resistant enterococcus infection. In yet another embodiment, the method includes administering to a subject an effective amount of the active compound against the methacillin-resistant staphylococcus infection.

The term "treat" refers to administering an effective amount of active compound to a subject that has a bacterial infection, or has symptoms and signs of such an infection, with the purpose to cure, heal, alleviate, relieve, alter, remedy, ameliorate, improve, or affect the infection, the symptoms and signs of the infection.

An "effective amount" refers to a dose of the active compound that is sufficient to eradicate or reduce the bacterial infection, which is measured by one or more of the following criteria: eradication or reduction of the bacteria by microbiological measures (such as blood culture) or serological measures (such as white blood cell count, serum C-reactive protein level), and resolution or improvement of clinical signs and symptoms (such as fever, tachycardia). Both in vivo and in vitro studies can be conducted by one skilled in the art to determine optimal administration routes and dose. The effective amount will vary depending upon several factors, including, but not limited to, the age and weight of the patient, route and frequency of administration, how advanced the disease state is, any co-morbidity, or the co-administration of other antimicrobial agents.

The term "administration" covers inhalation, topical, oral, rectal, implanted reservoir and parenteral (such as intravenous, intramuscular, subcutaneous, intra-articular, intra-synovial, cisternal, intrathecal, intrahepatic, intralesional and intracranial) delivery to a subject the active compound of the invention. Parenteral route of administration is preferred.

The composition for oral administration can be any orally acceptable dosage form including capsules, tablets, emulsions and aqueous suspensions, dispersions, and solutions. The oral composition may include sustained release properties as well as rapid delivery forms.

Topical application may be formulated in carriers such as hydrophobic or hydrophilic bases to form ointments, cream, lotions, in aqueous, oleaginous or alcoholic liquids to form paints or in dry diluents to form powders.

The parenteral compositions may take such forms as suspensions, solutions, or emulsions in oily or aqueous vehicles, and may contain various formulating agents. Alternatively, the active ingredient may be in powder form for reconstitution at the time of delivery with a suitable vehicle, such as sterile water.

In general, about 0.0625 mg to about 32 mg of a compound of formula (I) per kg of body weight per dose will be an effective dosage. The preferred dosage is about 0.125 mg to about 8 mg of compound of formula (I) per kg of body weight per dose, and more preferably about 0.5 mg to about 4 mg of compound of formula (I) per kg of body weight per dose. The treatment interval ranges from once per day to once per week. The dosage and treatment interval may vary somewhat depend upon the route of delivery and the condition of the patent, and determined by one skilled in the art.

The following examples further illustrate the present invention. These examples are intended merely to be illustrative of the present invention and are not to be construed as being limiting.

EXAMPLES

Example 1

Preparation of Compounds 14, 29, 30-32, 34 and 35

Compounds 14, 29, 30-32, 34 and 35 were enzymatically synthesized using: 0.5 mM of teicoplanin;

1. 10 mM of decylamine for compound 14; 10 mM of benzylamine for compound 29; 10 mM of 1-adamantanemethylamine for compound 30; 10 mM of 1-adamantaneamine for compound 31; 10 mM of 2-adamantaneamine for compound 32; 10 mM of propargylamine for compound 34; 10 mM of 5-azide pentylamine for compound 35; and 2. In the presence of 0.03 mM of Dbv29, 10 mM of Na(CN)BH$_3$ and 50% DMSO, the mixture was incubated at 37° C. overnight.

See Table 3 for product yields of compounds 14, 29, 30-32, 34 and 35.

Example 2

Preparation of compounds 15, 28 and 33

Compounds 15, 28 and 33 were enzymatically synthesized using:

1. 0.5 mM of teicoplanin;

2. 10 mM of hexylamine for compound 15; 10 mM of benzylamine for compound 28; and 10 mM of propargylamine for compound 33; and 3. In the presence of 0.03 mM of Dbv29, 10 mM of Na(CN)BH$_3$ and 50% DMSO, the mixture was incubated at 37° C. overnight.

See Table 3 for product yields of compounds 15, 28 and 33.

Example 3

Preparation of Compound 16

Compound 16 was enzymatically synthesized using 0.5 mM of teicoplanin and 10 mM Butylamine, in the presence of 0.03 mM of Dbv29. The mixture was incubated at 37° C. overnight. See Table 3 for the product yield of compound 16.

Example 4

Preparation of compound 17

Compound 17 was enzymatically synthesized using 0.5 mM of teicoplanin and 10 mM of aniline in the presence of 0.03 mM of Dbv29. The mixture was incubated at 37° C. overnight. See Table 3 for the product yield of compound 17.

Example 5

Preparation of Compound 18

Compound 18 was enzymatically synthesized using 0.5 mM of teicoplanin and 5 mM of octylamine in the presence of 0.03 mM of Dbv29, 5 mM of Na(CN)BH$_3$ and 50% DMSO. The mixture was incubated at 37° C. overnight. See Table 3 for the product yield of Compound 18.

Example 6

Preparation of Compound 19

Compound 19 was enzymatically synthesized using 0.5 mM of Teicoplanin and 5 mM of dodecylamine in the presence of 0.03 mM of Dbv29, 5 mM of Na(CN)BH$_3$ and 50% DMSO. The mixture was incubated at 37° C. overnight. See Table 3 for the product yield of compound 19.

Example 7

Preparation of compounds 20, 21, 22 and 23

(a) Hydrolyzing acetyl off N-acetyl glucosamine moiety: Combined 1 mM of teicoplanin with 0.02 mM of Dbv21, and the mixture was incubated at 37° C. for 6 hours.

(b) Acylation of glucosamine moiety with various CoA derivatives: Combined mixture (a) with 0.02 mM of Dbv8 and 1 mM of CoA derivatives (e.g. Butyryl CoA for compound 20, Hexanoyl CoA for compound 21, Octanoyl CoA for compound 22 and Decanoyl CoA for compound 23), and the mixture was incubated at 37° C. for 4 hours.

(c) Oxidation: Combined mixture (b) with 0.03 mM of Dbv29 and O$_2$ as the electron acceptor, and the mixture was incubated at 37° C. for 4 hours.

See Table 3 for product yields of compounds 20, 21, 22 and 23.

Example 8

Preparation of Compounds 24 and 25

(a) Hydrolyzing acetyl off N-acetyl glucosamine moiety: Combined 1 mM of teicoplanin with 0.02 mM of Dbv21, and the mixture was incubated at 37° C. for 6 hours.

(b) Acylation of glucosamine moiety with various CoA derivatives: Combined mixture (a) with 0.02 mM of Dbv8 and 1 mM of CoA derivatives (e.g. Hexanoyl CoA for compound 24 and Octanoyl CoA for compound 25), and the mixture was incubated at 37° C. for 4 hours.

(c) Oxidation: Combined mixture (b) with 0.03 mM of Dbv29, O$_2$ as the electron acceptor and 5 mM of hexylamine, and the mixture was incubated at 37° C. for 24 hours.

See Table 3 for product yields of compounds 24 and 25.

Example 9

Preparation of Compound 26

(a) Hydrolyzing acetyl off N-acetyl glucosamine moiety: Combined 1 mM of teicoplanin with 0.02 mM of Dbv21, and the mixture was incubated at 37° C. for 6 hours.

(b) Acylation of glucosamine moiety with CoA derivatives: Combined mixture (a) with 0.02 mM of Dbv8 and 1 mM of Hexanoyl CoA, and the mixture was incubated at 37° C. for 4 hours.

(c) Oxidation: Combined mixture (b) with 0.03 mM of Dbv29, O$_2$ as the electron acceptor, 5 mM of octylamine, 5 mM of Na(CN)BH$_3$ and 50% DMSO, and the mixture was incubated at 37° C. for 24 hours.

See Table 3 for the product yield of compound 26.

Example 10

Preparation of Compound 27

(a) Hydrolyzing acetyl off N-acetyl glucosamine moiety: Combined 1 mM of teicoplanin with 0.02 mM of Dbv21, and the mixture was incubated at 37° C. for 6 hours.

(b) Acylation of glucosamine moiety with CoA derivatives: Combined mixture (a) with 0.02 mM of Dbv8 and 1 mM of Octanoyl CoA, and the mixture was incubated at 37° C. for 4 hours.

(c) Oxidation: Combined mixture (b) with 0.03 mM of Dbv29, O$_2$ as the electron acceptor, 5 mM of dodecylamine, 5 mM of Na(CN)BH$_3$ and 50% DMSO, and the mixture was incubated at 37° C. for 24 hours.

See Table 3 for the product yield of compound 27.

The product yields of compounds 13 to 35 by Dbv29 are summarized in Table 3. The product yields were determined by HPLC, and yield=(peak area of aminated or amidated product)/(peak areas of aminated and amidated and oxidative products)×100%.

TABLE 3

| Compound | Coenzyme A derivative (Carbon No.) | Amine added | Product type: amide or amine | Yield % |
|---|---|---|---|---|
| 13 | — | — | — | 100 |
| 14 | — | H₂N-(CH₂)₉-CH₃ | Amine | 25 |
| 15 | — | H₂N-(CH₂)₆-CH₃ | Amide | 10 |

TABLE 3-continued

| Compound | Coenzyme A derivative (Carbon No.) | Amine added | Product type: amide or amine | Yield % |
|---|---|---|---|---|
| 16 (structure: sugar with aglycone, N-butyl amide, N-acyl isoalkyl chain) | — | H2N-butyl | Amide | <10 |
| 17 (structure: sugar with aglycone, N-phenyl amide, N-acyl isoalkyl chain) | — | H2N-phenyl (aniline) | Amide | 10 |
| 18 (structure: sugar with aglycone, N-octyl amine at C6, N-acyl isoalkyl chain) | — | H2N-octyl | Amine | 25 |

TABLE 3-continued
| Compound | Coenzyme A derivative (Carbon No.) | Amine added | Product type: amide or amine | Yield % |
|---|---|---|---|---|
| 19 | — | 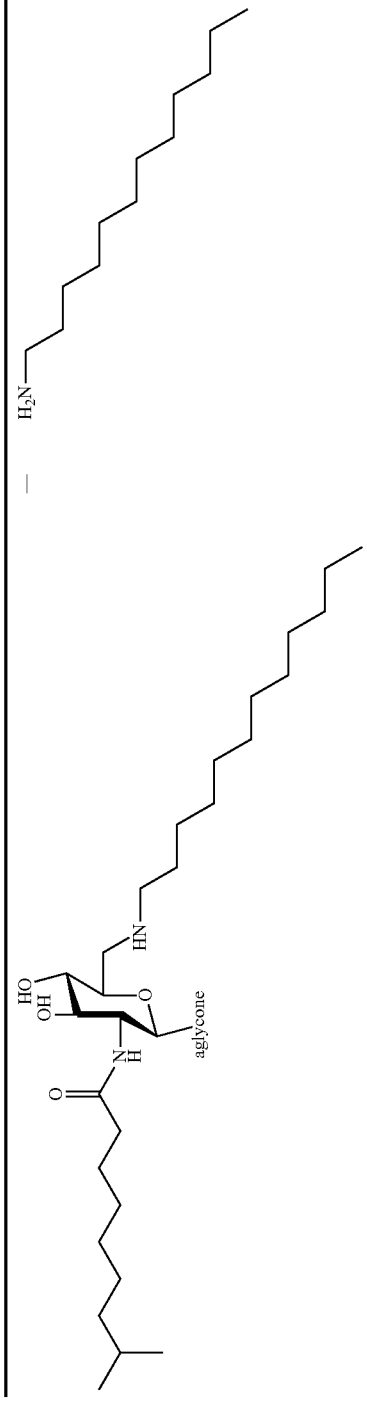 | Amine | 17 |
| 20 | C4 | — | — | 100 |
| 21 | C6 | — | — | 100 |

TABLE 3-continued

| Compound | Coenzyme A derivative (Carbon No.) | Amine added | Product type: amide or amine | Yield % |
|---|---|---|---|---|
| 22 | C8 | — | — | 100 |
| 23 | C10 | — | — | 100 |
| 24 | C6 | H₂N-hexyl | Amide | 10 |

TABLE 3-continued
| Compound | Coenzyme A derivative (Carbon No.) | Amine added | Product type: amide or amine | Yield % |
|---|---|---|---|---|
| 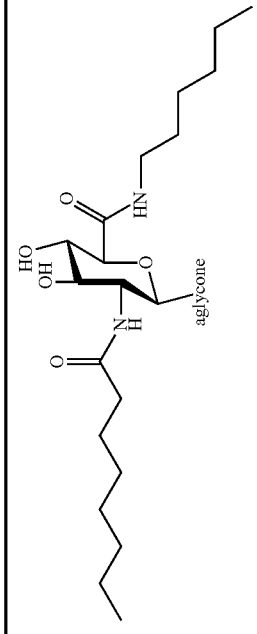 25 | C8 |  | Amide | 10 |
| 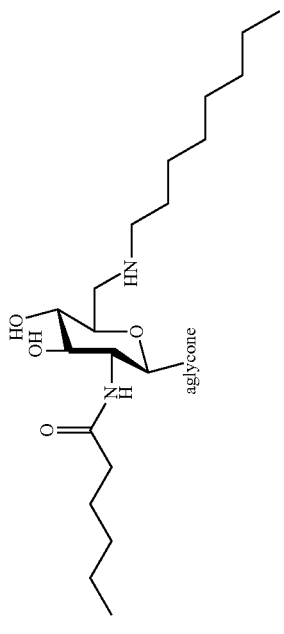 26 | C6 |  | Amine | 30 |
| 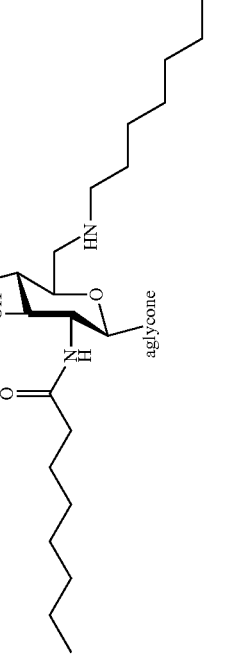 27 | C8 | 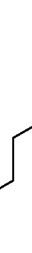 | Amine | 30 |

TABLE 3-continued
| Compound | Coenzyme A derivative (Carbon No.) | Amine added | Product type: amide or amine | Yield % |
|---|---|---|---|---|
| 28 | — | 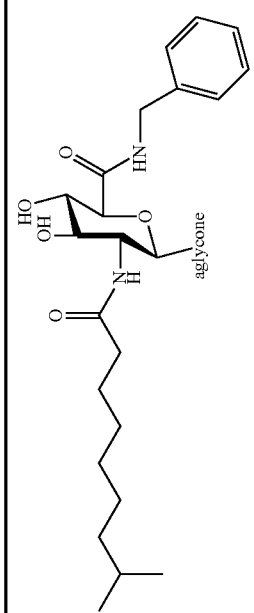 H₂N–CH₂–C₆H₅ | Amide | <10 |
| 29 | — | 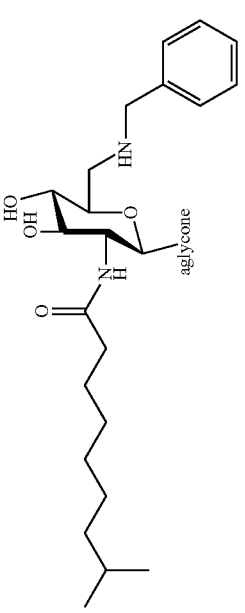 H₂N–CH₂–C₆H₅ | Amine | 46 |
| 30 | — | 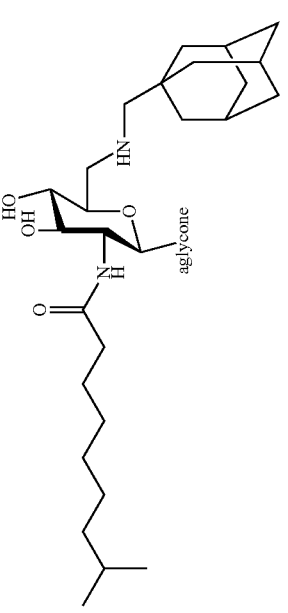 H₂N–CH₂–adamantyl | Amine | <10 |

TABLE 3-continued
| Compound | Coenzyme A derivative (Carbon No.) | Amine added | Product type: amide or amine | Yield % |
|---|---|---|---|---|
| 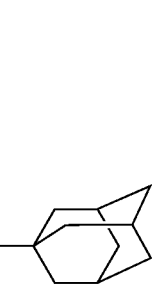 31 | — |  | Amine | <10 |
|  32 | — | 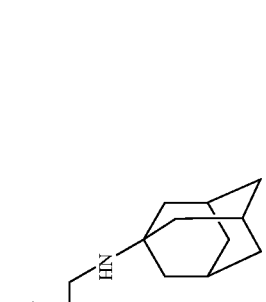 | Amine | <10 |
| 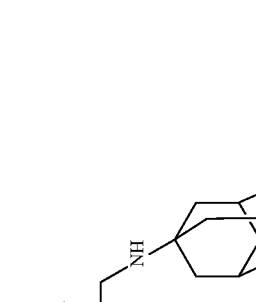 33 | — |  | Amide | <10 |

TABLE 3-continued
| Compound | Coenzyme A derivative (Carbon No.) | Amine added | Product type: amide or amine | Yield % |
|---|---|---|---|---|
| 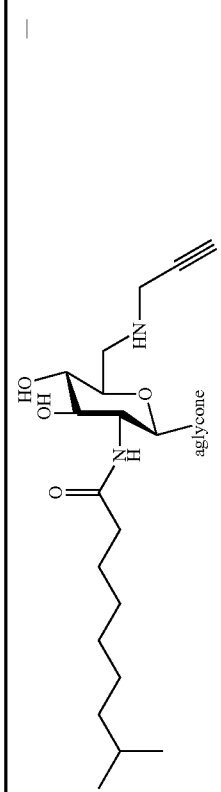 34 | — | H₂N—CH₂—C≡CH | Amine | <10 |
| 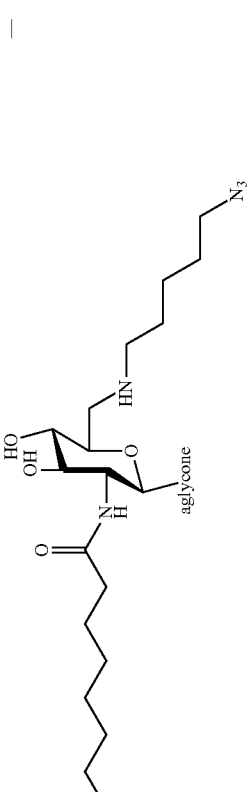 35 | — | H₂N—(CH₂)₆—N₃ | Amine | 25 |

Dbv8 was used to add various lengths of acyl side chains from corresponding CoA derivatives to the C2 amine group.

The preparation method of compounds 13 to 35 are summarized in Table 4.

TABLE 4

| Example No. | $R_1$ | $R_2$ | Scheme | Enzyme(s) used |
|---|---|---|---|---|
| 13 | $(CH_3)_2CH(CH_2)_6$ | $C(O)OH$ | I | Dbv 29 |
| 14 | $(CH_3)_2CH(CH_2)_6$ | $C(O)NH(CH_2)_9CH_3$ | III | Dbv 29 |
| 15 | $(CH_3)_2CH(CH_2)_6$ | $C(O)NH(CH_2)_5CH_3$ | II | Dbv 29 |
| 16 | $(CH_3)_2CH(CH_2)_6$ | $C(O)NH(CH_2)_3CH_3$ | II | Dbv 29 |
| 17 | $(CH_3)_2CH(CH_2)_6$ | $C(O)NH-C_6H_6$ | II | Dbv 29 |
| 18 | $(CH_3)_2CH(CH_2)_6$ | $CH_2NH(CH_2)_7CH_3$ | III | Dbv 29 |
| 19 | $(CH_3)_2CH(CH_2)_6$ | $CH_2NH(CH_2)_{11}CH_3$ | III | Dbv 29 |
| 20 | $CH_3(CH_2)_2$ | $C(O)OH$ | IV | Dbv 21, Dbv 8 and Dbv 29 |
| 21 | $CH_3(CH_2)_4$ | $C(O)OH$ | IV | Dbv 21, Dbv 8 and Dbv 29 |
| 22 | $CH_3(CH_2)_6$ | $C(O)OH$ | IV | Dbv 21, Dbv 8 and Dbv 29 |
| 23 | $CH_3(CH_2)_8$ | $C(O)OH$ | IV | Dbv 21, Dbv 8 and Dbv 29 |
| 24 | $CH_3(CH_2)_4$ | $C(O)NH(CH_2)_5CH_3$ | V | Dbv 21, Dbv 8 and Dbv 29 |
| 25 | $CH_3(CH_2)_6$ | $C(O)NH(CH_2)_5CH_3$ | V | Dbv 21, Dbv 8 and Dbv 29 |
| 26 | $CH_3(CH_2)_4$ | $CH_2NH(CH_2)_7CH_3$ | VI | Dbv 21, Dbv 8 and Dbv 29 |
| 27 | $CH_3(CH_2)_6$ | $CH_2NH(CH_2)_7CH_3$ | VI | Dbv 21, Dbv 8 and Dbv 29 |
| 28 | $(CH_3)_2CH(CH_2)_6$ | $C(O)NH-CH_2-C_6H_6$ | II | Dbv 29 |
| 29 | $(CH_3)_2CH(CH_2)_6$ | $CH_2-NH-CH_2-C_6H_6$ | III | Dbv 29 |
| 30 | $(CH_3)_2CH(CH_2)_6$ | $CH_2-NH-CH_2$-admantyl | III | Dbv 29 |
| 31 | $(CH_3)_2CH(CH_2)_6$ | $CH_2-NH$-admantyl | III | Dbv 29 |
| 32 | $(CH_3)_2CH(CH_2)_6$ | $CH_2-NH$-admantyl | III | Dbv 29 |
| 33 | $(CH_3)_2CH(CH_2)_6$ | $C(O)NH-CH_2-HC\equiv CH$ | II | Dbv 29 |
| 34 | $(CH_3)_2CH(CH_2)_6$ | $CH_2-NH-CH_2-HC\equiv CH$ | III | Dbv 29 |
| 35 | $(CH_3)_2CH(CH_2)_6$ | $CH_2-NH-(CH_2)_5-N_3$ | III | Dbv 29 |

Physiochemical properties of compounds 13 to 35 are summarized in Table 5.

TABLE 5

| Example No. | Molecular formula | Molecular Weight | Exact Mass | MS (m/z) | LC traces |
|---|---|---|---|---|---|
| 13 | $C_{88}H_{94}Cl_2N_9O_{34}$ | 1892.63 | 1890.53 | | 21.2 |
| 14 | $C_{98}H_{117}Cl_2N_{10}O_{32}$ | 2017.93 | 2015.72 | 2019.19 | 22.11 |
| 15 | $C_{94}H_{107}Cl_2N_{10}O_{33}$ | 1975.81 | 1973.64 | 1975.46 | 21.41 |
| 16 | $C_{92}H_{104}Cl_2N_{10}O_{33}$ | 1947.76 | 1946.61 | 1949.41 | 20.62 |
| 17 | $C_{94}H_{99}Cl_2N_{10}O_{33}$ | 1967.75 | 1965.58 | 1969.23 | |
| 18 | $C_{96}H_{114}Cl_2N_{10}O_{32}$ | 1989.88 | 1988.70 | 1991.50 | 20.75 |
| 19 | $C_{100}H_{121}Cl_2N_{10}O_{32}$ | 2045.98 | 2043.75 | 2047.11 | |
| 20 | $C_{82}H_{83}Cl_2N_9O_{34}$ | 1809.48 | 1807.44 | 1810.26 | 14.56 |
| 21 | $C_{84}H_{87}Cl_2N_9O_{34}$ | 1837.54 | 1835.47 | 1837.88 | 16.1 |
| 22 | $C_{86}H_{91}Cl_2N_9O_{34}$ | 1865.59 | 1863.50 | 1866.29 | 17.75 |
| 23 | $C_{88}H_{95}Cl_2N_9O_{34}$ | 1893.64 | 1891.54 | 1894.38 | 19.4 |
| 24 | $C_{90}H_{99}Cl_2N_{10}O_{33}$ | 1919.7 | 1917.58 | 1921.13 | |
| 25 | $C_{92}H_{103}Cl_2N_{10}O_{33}$ | 1947.76 | 1945.61 | 1948.22 | |
| 26 | $C_{92}H_{105}Cl_2N_{10}O_{32}$ | 1933.77 | 1931.63 | 1935.35 | |
| 27 | $C_{94}H_{109}Cl_2N_{10}O_{32}$ | 1961.83 | 1959.66 | 1963.52 | |
| 28 | $C_{95}H_{101}Cl_2N_{10}O_{33}$ | 1981.77 | 1979.59 | 1983.14 | 21.19 |
| 29 | $C_{95}H_{103}Cl_2N_{10}O_{32}$ | 1967.79 | 1965.61 | 1969.32 | 19.3 |
| 30 | $C_{99}H_{113}Cl_2N_{10}O_{32}$ | 2025.91 | 2023.69 | 1013.67 | |
| 31 | $C_{98}H_{111}Cl_2N_{10}O_{32}$ | 2011.88 | 2009.67 | 1006.56 | |
| 32 | $C_{98}H_{111}Cl_2N_{10}O_{32}$ | 2011.88 | 2009.67 | 1006.55 | |
| 33 | $C_{91}H_{98}Cl_2N_{10}O_{33}$ | 1930.7 | 1928.57 | 1931.29 | |
| 34 | $C_{91}H_{100}Cl_2N_{10}O_{32}$ | 1916.7 | 1914.59 | 1917.42 | |
| 35 | $C_{93}H_{107}Cl_2N_{13}O_{32}$ | 1989.81 | 1987.65 | 1990.25 | |

Example 11

In Vitro Anti-Bacterial Test

The antibacterial activity of the compounds of formula (I) can be demonstrated in vitro. The results of the antibacterial testing of vancomycin, teicoplanin and compounds 5-10, 13-15 and 29, using the Minimum Inhibition Concentrations (MICs) Test, are set forth in Table 6, which shows the MICs of vancomycin 1, teicoplanin 4, compounds 5-10, 13-15 and 29 against the testing bacterial strains (*Enterococcus Faecalis* and *Staphylococcus Aureus*).

TABLE 6

|  | Strains | | | | | | |
| --- | --- | --- | --- | --- | --- | --- | --- |
| Compound | E. faecalis ATCC 29302 | E. faecalis ATCC 33186 | E. faecalis ATCC 51299 | E. faecalis ATCC 51559 | E. faecalis ATCC 700221 | S. Aureus ATCC 29213 | S. Aureus ATCC 700699 |
| 1 (vancomycin) | 1 | 4 | >64 | >32 | >64 | 1 | 16 |
| 4 (Teicoplanin) | 0.125 | 0.25 | 0.5 | >32 | >32 | 0.5 | 8 |
| 5 | 8 | >32 | >32 | >32 | >32 | 16 | >32 |
| 6 | 8 | >32 | >32 | >32 | >32 | 16 | >32 |
| 7 | 8 | >32 | >32 | >32 | >32 | 8 | >32 |
| 8 | 2 | >32 | >32 | >32 | >32 | 4 | 32 |
| 9 | 0.125 | 0.25 | 0.25 | >32 | >32 | 0.5 | 8 |
| 10 | >64 | >64 | >64 | >64 | >64 | | |
| 13 (Oxo-Tei) | 0.125 | 0.25 | 0.25 | >32 | >32 | 0.5 | 8 |
| 14 | 0.5 | 0.5 | 0.5 | 1 | 4 | 4 | 16 |
| 15 | 0.0625 | 0.0625 | 0.125 | 8 | 32 | 2 | 16 |
| 29 | 0.125 | 0.25 | 0.5 | 0.25 | 2 | | |

1. The concentration unit is ug/ml. MIC was determined as given concentrations wherein there were no growths for given testing strains in duplicate.
2. E. faecalis (ATCC 29302) is a standard strain; E. faecalis (ATCC 33186) is an antibiotics sensitive strain; E. faecalis (ATCC 51299) is a low level VRE; E. faecalis (ATCC 51559) is a multidrug-resistant strain (VRE, ampicillin, ciprofloxacin, gentamicin, rifampicin, teicoplanin and vancomycin); E. faecalis (ATCC 700221) is a strain resistant to vancomycin; S. Aureus (ATCC 29213) is a methacillin-sensitive strain; and S. Aureus (ATCC 700699) is a strain resistant to methacillin, and reduced vancomycin susceptibility through thickening of the cell wall.

Compared to vancomycn and teicoplanin, the compounds of formula (I) showed significantly enhanced bactericidal activities against the five tested Enterococcus faecalis strains. In addition, it appears that compound 15 with a shorter chain is more effective against antibiotics-sensitive strains (e.g. ATCC 33186), whereas the longer-chain compound 14 is more effective against drug-resistant strains (e.g., ATCC 51559 and 70021). Strikingly, compound 29, tailored with benzylamine, is equally effective against the sensitive and resistant strains but the dosage is much lower compare to that of vancomycin and teicoplanin. Compound 29 complements the inadequacy of vancomycin against the Vancomycin-Resistant Enterococcus.

Compounds 9 and 13 are also effective in treating Staphylococcus Aureus and MRSA infections.

Example 13

In Vivo Animal Study

12 ICR female mice with an average body weight of 27 g to 30 g were used in this experiment. Mice had free access to water and food at all time. Sepsis was induced in mice by intravenous (i.v.) injection of $1.3 \times 10$ cfu/mouse of E. faecalis (ATCC 51559) on day 0. The mice were randomized into the following four treatment groups at the start of the experiment:

(a) Vancomycin (n=3);
(b) Teicoplanin (n=3);
(c) Compound 29 (n=3); and
(d) Saline (control).

Each mouse received 10 mg/kg/dose of the medication by intravenous route, twice a day from day 1 to day 3, for a total of 6 doses. Mice were anesthetized and blood was taken from the orbital sinus on day 1, day 2, and day 3. The blood sample was diluted with PBS, plated on Brain Heart infusion agar (BHI agar; Difico, Detroit, Mich., USA) and cultured for colony formation unit.

Figure 3A:
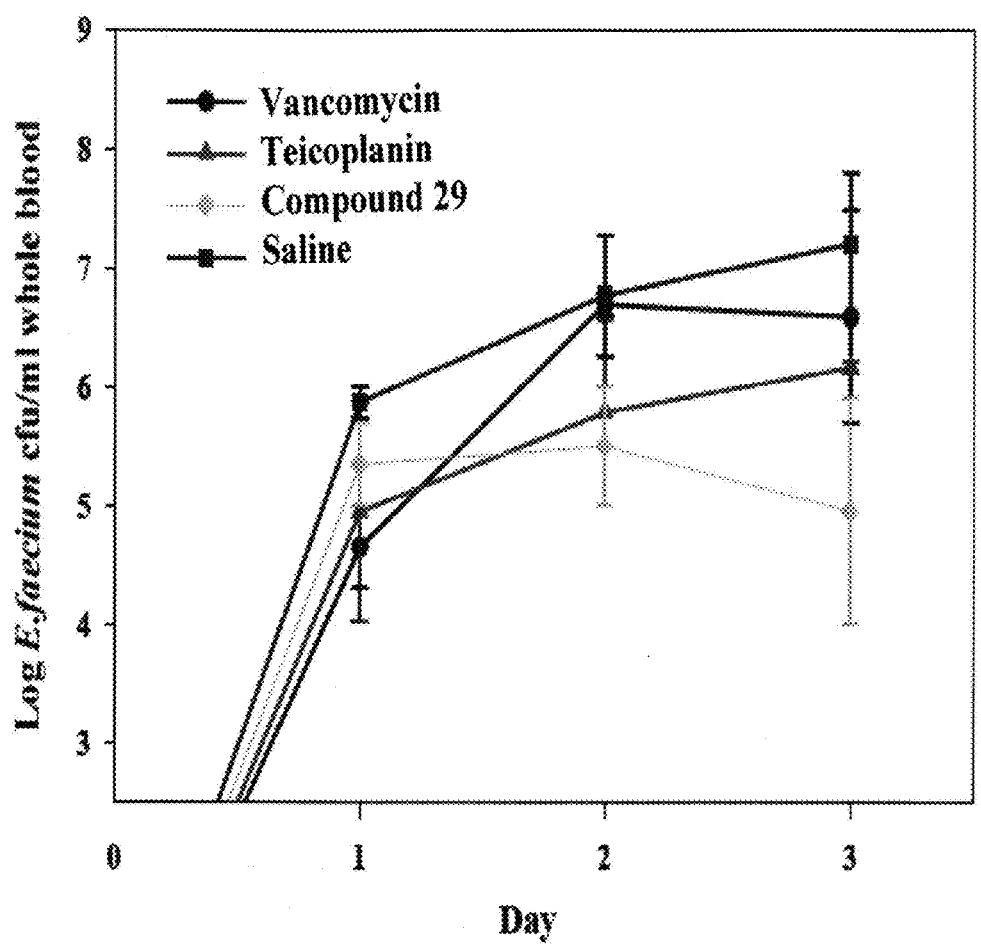
FIG. 3(a) shows the blood bacterial counts of mice infected by *E. faecalis* (ATCC 51559) and treated with vancomycin, teicoplanin, compound 29 of formula (I) or saline (control) over a 3-day period.
Figure 3B:
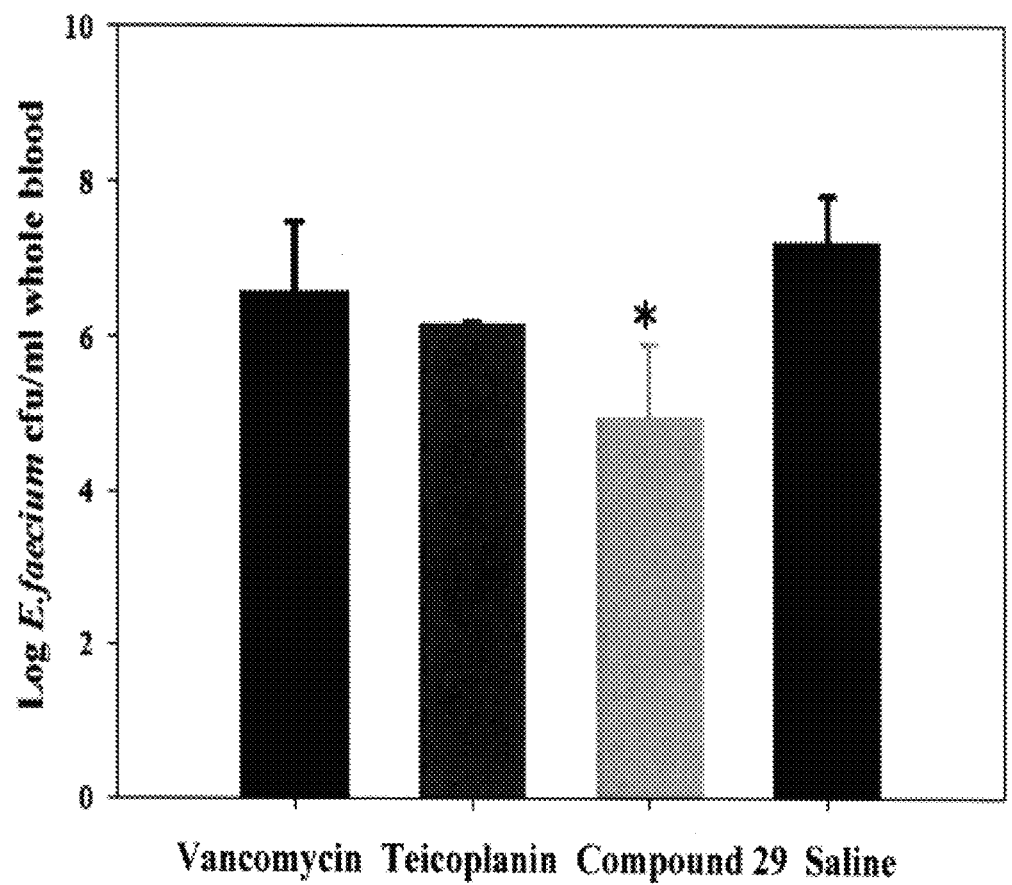
FIG. 3(b) shows the bacterial counts of mice on day 3 (the end of the treatment). The asterisk (*) indicates significant difference (P<0.05); data were expressed as mean+SD.

The results of the in vivo study are shown in FIGS. 3(a) and 3(b). Data were expressed as mean±SD and the statistical analysis was performed using SigmaStat®. Differences were considered to be significant if the P value was <0.05.

FIG. 3(a) shows the whole blood bacterial counts of mice infected by E. faecalis (ATCC 51559) and treated with vancomycin, teicoplanin, compound 29 or saline for three days. The bacterial counts for the control mice increased steadily over the 3-day period, while the bacterial counts in mice treated with vancomycin, teicoplanin and compound 29 were suppressed, but to different extents. These results show compound 29 is more efficacious than vancomycin and teicoplanin in treating E. faecalis infection. FIG. 3(b) shows the bacterial counts on day 3 (the end of the treatment). In general, these three drugs all show positive effects against the infection, but only compound 29 displays significant effect. The asterisk (*) indicates significant difference (P<0.05).

What is claimed is:

1. A compound of formula (I)

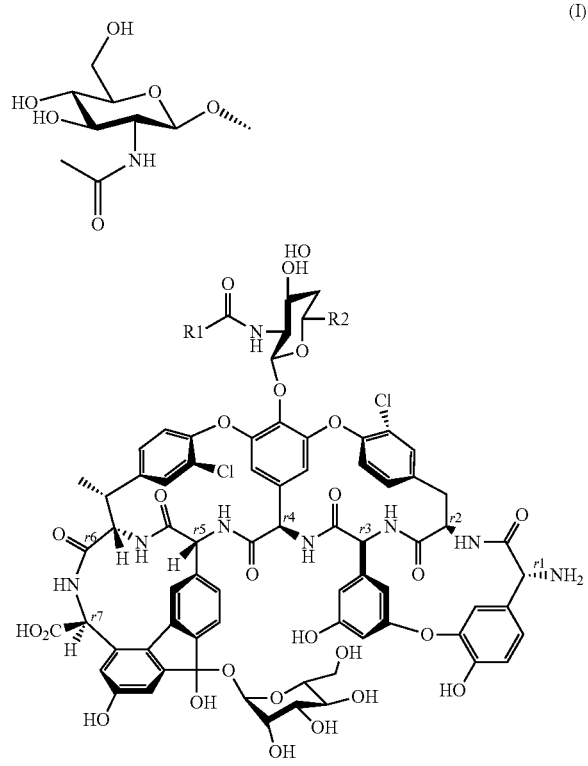

or a pharmaceutically acceptable salt thereof, $R_1$ is selected from the group consisting of aryl, alkyl, and alkynyl;

$R_2$ is selected from the group consisting of C(O)OH, C(O)NH—$R_3$, and $CH_2$—NH—$R_4$, provided that $R_1$ is not alkyl, when $R_2$ is C(O)OH or $CH_2$—NH—$R_4$;

$R_3$ is selected from the group consisting of aryl, alkyl, alkynyl;

$R_4$ is selected from the group consisting of aryl, alkyl, alkynyl, adamantyl, and $C_1$-$C_{10}$ azide.

2. The compound of claim 1, wherein $R_1$ is $C_1$-$C_{15}$ alkyl.

3. The compound of claim 1, wherein $R_1$ is $(CH_3)_2CH(CH_2)_6$; $CH_3(CH_2)_2$; $CH_3(CH_2)_4$; $CH_3(CH_2)_6$ or $CH_3(CH_2)_8$.

4. The compound of claim 1, wherein $R_3$ is phenyl, benzyl, $C_1$-$C_{10}$ alkyl or $C_1$-$C_{10}$ alkynyl.

5. The pharmaceutical composition of claim 1, wherein $R_3$ is $(CH_2)_3CH_3$, $(CH_2)_5CH_3$ or $CH_2HC$=CH.

6. The compound of claim 1, wherein $R_4$ is benzyl, $(CH_2)_7CH_3$, $(CH_2)_{11}CH_3$, adamantyl, adamantyl-$CH_2$, $CH_2$—HC=CH and $(CH_2)_5N_3$.

7. A pharmaceutical composition, comprising a compound of formula (I):

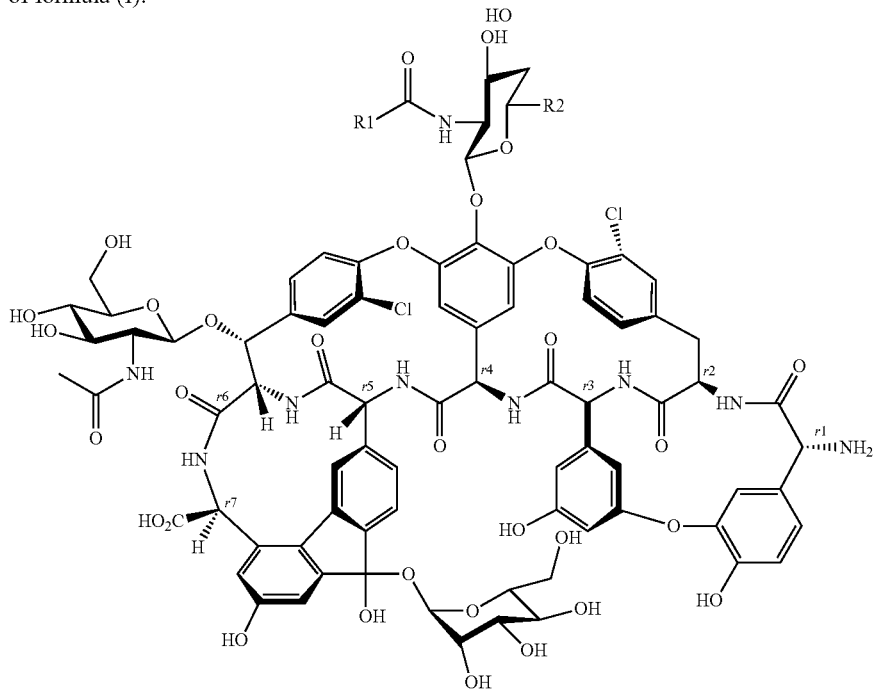

or a pharmaceutically acceptable salt thereof, $R_1$ is selected from the group consisting of aryl, alkyl, and alkynyl;

$R_2$ is selected from the group consisting of C(O)OH, C(O)NH—$R_3$, and CH$_2$—NH—$R_4$, provided that $R_1$ is not alkyl, when $R_2$ is C(O)OH or CH$_2$—NH—$R_4$;

$R_3$ is selected from the group consisting of aryl, alkyl, alkynyl;

$R_4$ is selected from the group consisting of aryl, alkyl, alkynyl, adamantyl, and $C_1$-$C_{10}$ azide, and a pharmaceutically acceptable carrier.

8. The pharmaceutical composition of claim 7, wherein $R_1$ is $C_1$-$C_{15}$ alkyl.

9. The pharmaceutical composition of claim 7, wherein $R_1$ is (CH$_3$)$_2$CH(CH$_2$)$_6$; CH$_3$(CH$_2$)$_2$; CH$_3$(CH$_2$)$_4$; CH$_3$(CH$_2$)$_6$ or CH$_3$(CH$_2$)$_8$.

10. The pharmaceutical composition of claim 7, wherein $R_3$ is phenyl, benzyl, $C_1$-$C_{10}$ alkyl or $C_1$-$C_{10}$ alkynyl.

11. The pharmaceutical composition of claim 7, wherein $R_3$ is (CH$_2$)$_3$CH$_3$, (CH$_2$)$_5$CH$_3$ or CH$_2$HC≡CH.

12. The pharmaceutical composition of claim 7, wherein $R_4$ is benzyl, (CH$_2$)$_7$CH$_3$, (CH$_2$)$_{11}$CH$_3$, adamantyl, adamantyl-CH$_2$, CH$_2$—HC≡CH and (CH$_2$)$_5$N$_3$.

13. A method of making compound of formula (I):

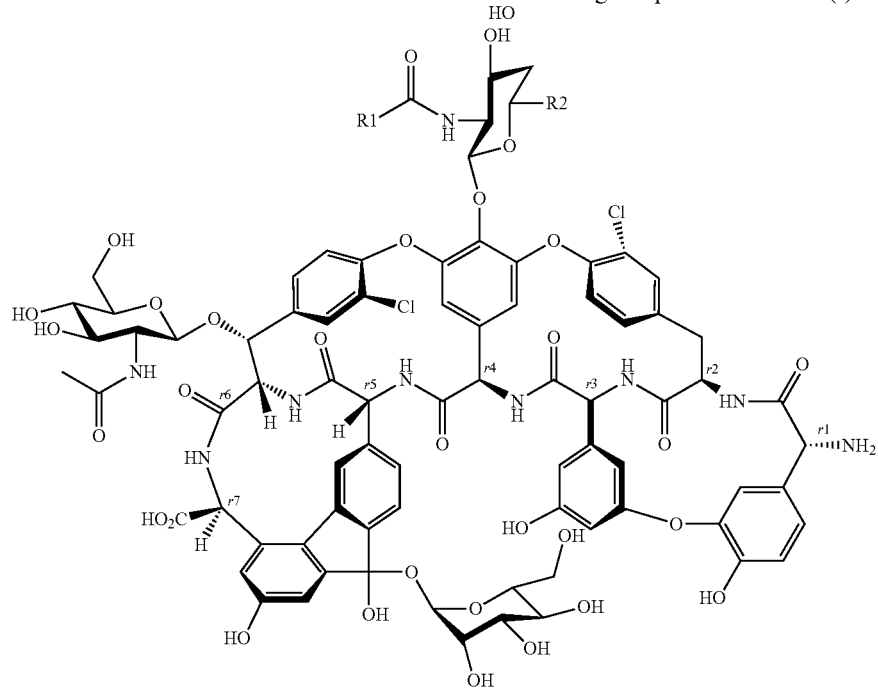

wherein
- R₁ is selected from the group consisting of aryl, alkyl, alkynyl;
- R₂ is selected from the group consisting of C(O)OH, C(O)NH—R₃, and CH₂—NH—R₄, provided that R₁ is not alkyl, when R₂ is C(O)OH or CH₂—NH—R₄;
- R₃ is selected from the group consisting of aryl, alkyl, alkynyl;
- R₄ is selected from the group consisting of aryl, alkyl, alkynyl, adamantyl, and $C_1$-$C_{10}$azide, comprising the steps of:
(a) binding teicoplanin to Dbv29; and
(b) incubating the mixture (a).

14. The method of claim 13, further comprising adding alkylamine prior to the incubation.

15. The method of claim 13, further comprising adding an organic solvent prior to incubating the mixture.

16. The method of claim 13, further comprising adding a reducing agent prior to incubating the mixture.

17. The method of claim 13, wherein the incubation is at about 30° C. to about 40° C.

18. The method of claim 13, further comprising adding Dbv 21 to teicoplanin.

19. The method of claim 13, further comprising adding Dbv 8 to teicoplanin.

20. The method of claim 13, further comprising adding a Co A derivative.

21. The method of claim 20, wherein the Co A derivative is one or more of the following: acetyl CoA, propionyl CoA, butyryl CoA, hexanoyl CoA, octanoyl CoA, decanoyl CoA, lauroyl CoA, myristoyl CoA, palmitoyl CoA, crotonyl CoA, isobutyryl CoA, isovaleryl CoA, malonyl CoA, succinyl CoA, glutaryl CoA, methylmalonyl CoA, acetoacetyl CoA, benzoyl CoA, phenylacetyl CoA, biphenylacetyl CoA, or naphthoacetyl CoA.

22. The method of claim 13, wherein the incubation time is about 1 hour to about 24 hours for each mM of teicoplanin used.

23. The method of claim 13, wherein the incubation time is about 2 hours to about 12 hours for each mM of teicoplanin used.

24. The method of claim 13, further comprising adding an electron acceptor.

25. The method of claim 24, wherein the electron acceptor is $O_2$.

26. A method for treating a Gram-positive bacterial infection in a subject, comprising the steps of:
   administering to the subject in thereof an effective amount of compound of formula (I) to treat said bacterial infection;

(I)

wherein
- R₁ is selected from the group consisting of aryl, alkyl, alkynyl;
- R₂ is selected from the group consisting of C(O)OH, C(O)NH—R₃, and CH₂—NH—R₄, provided that R₁ is not alkyl, when R₂ is C(O)OH or CH₂—NH—R₄;
- wherein R₃ is selected from the group consisting of aryl, alkyl, alkynyl;
- R₄ is selected from the group consisting of aryl, alkyl, alkynyl, adamantyl, and $C_1$-$C_{10}$azide.

27. The method of claim 26, wherein the effective amount is about 0.0625 to about 32 mg of compound of formula (I) per kg of body weight per dose.

28. The method of claim 26, wherein the effective amount is about 0.125 mg to about 8 mg of compound of formula (I) per kg of body weight per dose.

29. The method of claim 26, wherein the compound of formula (I) is administered once per day to once per week.

30. The method of claim 26, wherein said administering is by parenteral route.

* * * * *